US008318149B2

(12) United States Patent
Carette et al.

(10) Patent No.: US 8,318,149 B2
(45) Date of Patent: Nov. 27, 2012

(54) REPLICATION COMPETENT VIRUSES CAPABLE OF SILENCING VIRUS INHIBITORY FACTOR EXPRESSION

(75) Inventors: Jan E. Carette, Cambridge, MA (US); Victor W. van Beusechem, Amsterdam (NL)

(73) Assignee: Vereniging voor christelijik hoger onderwijs, wetenschappelijk onderzoek en patientenzorg, Amsterdam (NL)

(*) Notice: Subject to any disclaimer, the term of this patent is extended or adjusted under 35 U.S.C. 154(b) by 820 days.

(21) Appl. No.: 11/545,095

(22) Filed: Oct. 9, 2006

(65) Prior Publication Data

US 2007/0122385 A1 May 31, 2007

Related U.S. Application Data

(63) Continuation of application No. PCT/EP2005/004152, filed on Apr. 15, 2005.

(51) Int. Cl.
*C12N 15/113* (2010.01)
*C12N 15/11* (2006.01)
*C12N 15/09* (2006.01)
*A61K 48/00* (2006.01)

(52) U.S. Cl. ................ 424/93.2; 435/320.1; 424/93.6; 536/24.5; 536/23.1

(58) Field of Classification Search .................. None
See application file for complete search history.

(56) References Cited

U.S. PATENT DOCUMENTS

| | | | |
|---|---|---|---|
| 7,776,525 B2 * | 8/2010 | Kuroda et al. ............ | 435/6.17 |
| 2002/0173026 A1 * | 11/2002 | Wettstein et al. ............ | 435/199 |
| 2003/0138405 A1 * | 7/2003 | Fueyo et al. ............... | 424/93.2 |
| 2003/0157030 A1 * | 8/2003 | Davis et al. ................ | 424/46 |
| 2003/0176350 A1 * | 9/2003 | DePinho ................... | 514/12 |
| 2003/0203372 A1 * | 10/2003 | Ward et al. ................ | 435/6 |
| 2004/0002060 A1 * | 1/2004 | Kaleko et al. .............. | 435/5 |
| 2004/0028654 A1 * | 2/2004 | Ji et al. ..................... | 424/93.2 |
| 2005/0220765 A1 | 10/2005 | Van Beusechem et al. | |
| 2007/0122385 A1 | 5/2007 | Carette et al. | |
| 2008/0064647 A1 * | 3/2008 | Guo et al. .................. | 514/44 |

FOREIGN PATENT DOCUMENTS

| | | |
|---|---|---|
| EP | 1 439 227 | 7/2004 |
| WO | WO 03/057892 | 7/2003 |
| WO | WO03062394 | 7/2003 |
| WO | WO03080638 | 10/2003 |
| WO | WO 2004/013355 | 2/2004 |
| WO | WO 2004/063374 | 7/2004 |
| WO | WO 2005/100576 A2 | 10/2005 |

OTHER PUBLICATIONS van Beusechem et al, Conditionally Replicative Adenovirus Expressing p53 Exhibits Enhanced Oncolytic Potency, Cancer Research 62, 6165-6171, Nov. 1, 2002.*
Tortora et al, A novel MDM2 anti-sense oligonucleotide has anti-tumor activity and potentiates cytotoxic drugs acting by different mechanisms in human colon cancer, Int J Cancer. Dec. 1, 2000;88(5):804-9.*
Arts te al, Adenoviral Vectors Expressing siRNAs for Discovery and Validation of Gene Function, Genome Res. 2003 13: 2325-2332.*
Arts et al., "Adenoviral Vectors Expressing siRNAs for Discovery and Validation of Gene Function," Genome Research, Sep. 15, 2003, pp. 2325-2332, vol. 13.
Carette et al., "Conditionally Replicating Adenoviruses Expressing Short Hairpin RNA's Silence the Expression of a Target Gene in Cancer," Cancer Research, Apr. 15, 2004, pp. 2663-2667, vol. 64.
Paddison et al., "Short hairpin RNAs (shRNAs) induce sequence-specific silencing in mammalian cells," Genes and Development 2002, pp. 948-958, vol. 16.
Vickers et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.
Ding et al., RNA silencing: a conserved antiviral immunity of plants and animals, Virus Research, 1-7 (2004).
Michiels et al., Arrayed adenoviral expression libraries for functional screening, Nature Biotechnology, vol. 20, 1154-1157, Nov. 2002.
Graat et al., Enhanced tumor cell kill by combined treatment with a small-molecule antagonist of mouse double minute 2 and adenoviruses encoding p53, Mol. Cancer Ther. 2007;6(5), 1552-1561, May 2007.
Gutch et al., Repression of the interferon signal transduction pathway by the adenovirus E1A oncogene, Proc. Natl. Acad. Sci. USA, vol. 88, pp. 7913-7917, Sep. 1991.
Jiang et al., Selective silencing of viral gene expression in HPV-positive human cervical carcinoma cells treated with siRNA, a primer of RNA interference, Oncogene (2002) 21, 6041-6048.
Li et al., Interferon antagonist proteins of influenza and vaccinia viruses are suppressors of RNA silencing, PNAS, vol. 101, No. 5, 1350-1355, Feb. 2004.
Suzuki, The Presence of the Adenovirus E3 Region Improves the Oncolytic Potency of Conditionally Replicative Adenoviruses, Clinical Cancer Research, vol. 8, 3348-3359, Nov. 2002.
Yamasaki, Cytoplasmic destruction of p53 by the endoplasmic reticulum-resident ubiquitin ligase 'Synoviolin', The EMBO Journal, vol. 28, No. 1, 113-122, 2007.

* cited by examiner

*Primary Examiner* — Maria Marvich
(74) *Attorney, Agent, or Firm* — Hoffmann & Baron, LLP

(57) ABSTRACT

Described is a replication-competent virus capable of replication and having lytic capacity in target cells. The virus comprises in the genome thereof, at least one DNA sequence coding for a silencing factor functional in reducing expression of a target gene in the target cells, operably linked to one or more expression control sequences, functional in the target cells. The use thereof in the preparation of a medicament and the use thereof in a method for lysing target cells expressing a virus inhibitory factor are also described.

11 Claims, 6 Drawing Sheets

SEQUENCE LISTING

<160> NUMBER OF SEQ ID NOS: 38

<210> SEQ ID NO 1
<211> LENGTH: 30
<212> TYPE: DNA
<213> ORGANISM: Artificial
<220> FEATURE:
<223> OTHER INFORMATION: PCR Primer

<400> SEQUENCE: 1
gaggtcgacg cgatcgataa gcttgatatc                30

<210> SEQ ID NO 2
<211> LENGTH: 28
<212> TYPE: DNA
<213> ORGANISM: Artificial
<220> FEATURE:
<223> OTHER INFORMATION: PCR Primer

<400> SEQUENCE: 2
tagaactagt cgatcgcccg ggctgcag                28

<210> SEQ ID NO 3
<211> LENGTH: 72
<212> TYPE: DNA
<213> ORGANISM: Artificial
<220> FEATURE:
<223> OTHER INFORMATION: Synthetic oligonucleotide

<400> SEQUENCE: 3
gattccaatt cagcgggagc cacctgatga agcttgatcg ggtggctctc gctgagttgg    60
aatccatttt tt                                                       72

<210> SEQ ID NO 4
<211> LENGTH: 78
<212> TYPE: DNA
<213> ORGANISM: Artificial
<220> FEATURE:
<223> OTHER INFORMATION: Synthetic oligonucleotide

<400> SEQUENCE: 4
gatcaaaaaa tggattccaa ctcagcgaga gccacccgat caagcttcat caggtggctc    60
ccgctgaatt ggaatccg                                                 78

<210> SEQ ID NO 5
<211> LENGTH: 30
<212> TYPE: DNA
<213> ORGANISM: Artificial
<220> FEATURE:
<223> OTHER INFORMATION: PCR Primer

<400> SEQUENCE: 5
ccagaagagc tcgcaacgtg gcatctgcta                                    30

<210> SEQ ID NO 6
<211> LENGTH: 29
<212> TYPE: DNA
<213> ORGANISM: Artificial
<220> FEATURE:
<223> OTHER INFORMATION: PCR Primer

<400> SEQUENCE: 6
gtttggagag ctcctgggca caatgaggc                                     29

<210> SEQ ID NO 7
<211> LENGTH: 26
<212> TYPE: DNA
<213> ORGANISM: Artificial
<220> FEATURE:
<223> OTHER INFORMATION: PCR Primer

<400> SEQUENCE: 7
acaacggtac cgaacttaag ctgcag                                        26

<210> SEQ ID NO 8
<211> LENGTH: 27
<212> TYPE: DNA
<213> ORGANISM: Artificial
<220> FEATURE:
<223> OTHER INFORMATION: PCR Primer

<400> SEQUENCE: 8
ccgaaaggta ccacctggat ccttatc                                       27

<210> SEQ ID NO 9
<211> LENGTH: 29
<212> TYPE: DNA
<213> ORGANISM: Artificial

```
<220> FEATURE:
<223> OTHER INFORMATION: Mutated target recognition site of firefly
      luciferase

<400> SEQUENCE: 9
accaggttgc ccctgctgag ttggaatcg                                          29

<210> SEQ ID NO 10
<211> LENGTH: 27
<212> TYPE: DNA
<213> ORGANISM: Artificial
<220> FEATURE:
<223> OTHER INFORMATION: Synthetic oligonucleotide

<400> SEQUENCE: 10
accaggttgc ccctgctgag ttggaat                                            27

<210> SEQ ID NO 11
<211> LENGTH: 29
<212> TYPE: DNA
<213> ORGANISM: Artificial
<220> FEATURE:
<223> OTHER INFORMATION: Synthetic oligonucleotide

<400> SEQUENCE: 11
cgattccaac tcagcagggg caacctggt                                          29

<210> SEQ ID NO 12
<211> LENGTH: 64
<212> TYPE: DNA
<213> ORGANISM: Artificial
<220> FEATURE:
<223> OTHER INFORMATION: Synthetic oligonucleotide

<400> SEQUENCE: 12
gatcccccta acactgggtt atacaattca agagattgta taacccagtg ttagtttttg        60
gaaa                                                                    64

<210> SEQ ID NO 13
<211> LENGTH: 64
<212> TYPE: DNA
<213> ORGANISM: Artificial
<220> FEATURE:
<223> OTHER INFORMATION: Synthetic oligonucleotide

<400> SEQUENCE: 13
agcttttcca aaaactaaca ctgggttata caatctcttg aattgtataa cccagtgtta        60
gggg                                                                    64

<210> SEQ ID NO 14
<211> LENGTH: 52
<212> TYPE: DNA
<213> ORGANISM: Artificial
<220> FEATURE:
<223> OTHER INFORMATION: Synthetic oligonucleotide

<400> SEQUENCE: 14
ggcggctttg ccaagtgctt ctcgagaagc acttggcaaa gccgcccttt tt                52

<210> SEQ ID NO 15
<211> LENGTH: 58
<212> TYPE: DNA
<213> ORGANISM: Artificial
<220> FEATURE:
<223> OTHER INFORMATION: Synthetic oligonucleotide
```

```
<400> SEQUENCE: 15
gatcaaaaag ggcggctttg ccaagtgctt ctcgagaagc acttggcaaa gccgcccg        58

<210> SEQ ID NO 16
<211> LENGTH: 52
<212> TYPE: DNA
<213> ORGANISM: Artificial
<220> FEATURE:
<223> OTHER INFORMATION: Synthetic oligonucleotide

<400> SEQUENCE: 16
gccgcctccc tcatccagaa ctcgagttct ggatgaggga ggcggccttt tt              52

<210> SEQ ID NO 17
<211> LENGTH: 58
<212> TYPE: DNA
<213> ORGANISM: Artificial
<220> FEATURE:
<223> OTHER INFORMATION: Synthetic oligonucleotide

<400> SEQUENCE: 17
gatcaaaaag gccgcctccc tcatccagaa ctcgagttct ggatgaggga ggcggccg        58

<210> SEQ ID NO 18
<211> LENGTH: 56
<212> TYPE: DNA
<213> ORGANISM: Artificial
<220> FEATURE:
<223> OTHER INFORMATION: Synthetic oligonucleotide

<400> SEQUENCE: 18
atgaagaaga tcaccctcct tactcgagta aggagggtga tcttcttcat cttttt          56

<210> SEQ ID NO 19
<211> LENGTH: 62
<212> TYPE: DNA
<213> ORGANISM: Artificial
<220> FEATURE:
<223> OTHER INFORMATION: Synthetic oligonucleotide

<400> SEQUENCE: 19
gatcaaaaag atgaagaaga tcaccctcct tactcgagta aggagggtga tcttcttcat      60
cg                                                                    62

<210> SEQ ID NO 20
<211> LENGTH: 56
<212> TYPE: DNA
<213> ORGANISM: Artificial
<220> FEATURE:
<223> OTHER INFORMATION: Synthetic oligonucleotide

<400> SEQUENCE: 20
gaagctttcc tcgagatcca cttcctgtca tggatctcga ggaaagcttc cttttt          56

<210> SEQ ID NO 21
<211> LENGTH: 62
<212> TYPE: DNA
<213> ORGANISM: Artificial
<220> FEATURE:
<223> OTHER INFORMATION: Synthetic oligonucleotide

<400> SEQUENCE: 21
gatcaaaaag gaagctttcc tcgagatcca tgacaggaag tggatctcga ggaaagcttc      60
cg                                                                    62
```

```
<210> SEQ ID NO 22
<211> LENGTH: 56
<212> TYPE: DNA
<213> ORGANISM: Artificial
<220> FEATURE:
<223> OTHER INFORMATION: Synthetic oligonucleotide

<400> SEQUENCE: 22
gcatcgagca gcacatggat cttcctgtca atccatgtgc tgctcgatgc ctttttt      56

<210> SEQ ID NO 23
<211> LENGTH: 62
<212> TYPE: DNA
<213> ORGANISM: Artificial
<220> FEATURE:
<223> OTHER INFORMATION: Synthetic oligonucleotide

<400> SEQUENCE: 23
gatcaaaaag gcatcgagca gcacatggat tgacaggaag atccatgtgc tgctcgatgc   60
cg                                                                 62

<210> SEQ ID NO 24
<211> LENGTH: 56
<212> TYPE: DNA
<213> ORGANISM: Artificial
<220> FEATURE:
<223> OTHER INFORMATION: Synthetic oligonucleotide

<400> SEQUENCE: 24
ctcgccagga gaagcggttt cttcctgtca aaaccgcttc tcctggcgag ctttttt      56

<210> SEQ ID NO 25
<211> LENGTH: 62
<212> TYPE: DNA
<213> ORGANISM: Artificial
<220> FEATURE:
<223> OTHER INFORMATION: Synthetic oligonucleotide

<400> SEQUENCE: 25
gatcaaaaag ctcgccagga gaagcggttt tgacaggaag aaaccgcttc tcctggcgag   60
cg                                                                 62

<210> SEQ ID NO 26
<211> LENGTH: 20
<212> TYPE: DNA
<213> ORGANISM: Artificial
<220> FEATURE:
<223> OTHER INFORMATION: Synthetic oligonucleotide

<400> SEQUENCE: 26
tcaggactag tggaatgtac                                              20

<210> SEQ ID NO 27
<211> LENGTH: 20
<212> TYPE: DNA
<213> ORGANISM: Artificial
<220> FEATURE:
<223> OTHER INFORMATION: Synthetic oligonucleotide

<400> SEQUENCE: 27
attccactag tcctgagtac                                              20

<210> SEQ ID NO 28
<211> LENGTH: 56
<212> TYPE: DNA
```

<213> ORGANISM: Artificial
<220> FEATURE:
<223> OTHER INFORMATION: Synthetic oligonucleotide

<400> SEQUENCE: 28
ctgcacctga cgcccttcac cttcctgtca gtgaagggcg tcaggtgcag ctttttt    56

<210> SEQ ID NO 29
<211> LENGTH: 62
<212> TYPE: DNA
<213> ORGANISM: Artificial
<220> FEATURE:
<223> OTHER INFORMATION: Synthetic oligonucleotide

<400> SEQUENCE: 29
gatcaaaaag ctgcacctga cgcccttcac tgacaggaag gtgaagggcg tcaggtgcag    60
cg    62

<210> SEQ ID NO 30
<211> LENGTH: 56
<212> TYPE: DNA
<213> ORGANISM: Artificial
<220> FEATURE:
<223> OTHER INFORMATION: Synthetic oligonucleotide

<400> SEQUENCE: 30
ggaggattgt ggccttcttt cttcctgtca aaagaaggcc acaatcctcc ctttttt    56

<210> SEQ ID NO 31
<211> LENGTH: 62
<212> TYPE: DNA
<213> ORGANISM: Artificial
<220> FEATURE:
<223> OTHER INFORMATION: Synthetic oligonucleotide

<400> SEQUENCE: 31
gatcaaaaag ggaggattgt ggccttcttt tgacaggaag aaagaaggcc acaatcctcc    60
cg    62

<210> SEQ ID NO 32
<211> LENGTH: 56
<212> TYPE: DNA
<213> ORGANISM: Artificial
<220> FEATURE:
<223> OTHER INFORMATION: Synthetic oligonucleotide

<400> SEQUENCE: 32
gatccaggat aacggaggct cttcctgtca agcctccgtt atcctggatc ctttttt    56

<210> SEQ ID NO 33
<211> LENGTH: 62
<212> TYPE: DNA
<213> ORGANISM: Artificial
<220> FEATURE:
<223> OTHER INFORMATION: Synthetic oligonucleotide

<400> SEQUENCE: 33
gatcaaaaag gatccaggat aacggaggct tgacaggaag agcctccgtt atcctggatc    60
cg    62

<210> SEQ ID NO 34
<211> LENGTH: 61
<212> TYPE: DNA
<213> ORGANISM: Artificial
<220> FEATURE:

```
<223> OTHER INFORMATION: Synthetic oligonucleotide

<400> SEQUENCE: 34
ggcaggcgca atcttcgcat ttcttttttc caggaatcta gagatatcga gctcaataaa    60
g                                                                    61

<210> SEQ ID NO 35
<211> LENGTH: 69
<212> TYPE: DNA
<213> ORGANISM: Artificial
<220> FEATURE:
<223> OTHER INFORMATION: Synthetic oligonucleotide

<400> SEQUENCE: 35
aattctttat tgagctcgat atctctagat tcctggaaaa aagaaatgcg aagattgcgc    60
ctgcctgca                                                            69

<210> SEQ ID NO 36
<211> LENGTH: 33
<212> TYPE: DNA
<213> ORGANISM: Artificial
<220> FEATURE:
<223> OTHER INFORMATION: PCR Primer

<400> SEQUENCE: 36
gggtctagag ccaccatgga agacgccaaa aac                                 33

<210> SEQ ID NO 37
<211> LENGTH: 30
<212> TYPE: DNA
<213> ORGANISM: Artificial
<220> FEATURE:
<223> OTHER INFORMATION: PCR Primer

<400> SEQUENCE: 37
cccgagctcc ttacacggcg atctttccgc                                     30

<210> SEQ ID NO 38
<211> LENGTH: 8
<212> TYPE: PRT
<213> ORGANISM: Artificial
<220> FEATURE:
<223> OTHER INFORMATION: Adenoviral E1A epitope

<400> SEQUENCE: 38

Leu Thr Cys His Glu Ala Gly Phe
1               5
```

REPLICATION COMPETENT VIRUSES CAPABLE OF SILENCING VIRUS INHIBITORY FACTOR EXPRESSION

CROSS-REFERENCE TO RELATED APPLICATIONS

This application is a continuation of PCT International Patent Application No. PCT/EP2005/004152, filed on Apr. 15, 2005, designating the United States of America, and published, in English, as PCT International Publication No. WO 2005/100576 A2 on Oct. 27, 2005, which application claims priority to European Patent Application Serial No. 04076154.6, filed Apr. 15, 2004, the contents of the entirety of each of which are hereby incorporated herein by this reference.

TECHNICAL FIELD

The present invention relates to the fields of genetic modification, biotechnology and medicine. In particular, the invention provides recombinant viruses, in particular, adenoviruses with a potency to lyse cells in which they replicate and to suppress expression of one or more target genes in the cells in which they replicate.

BACKGROUND OF THE INVENTION

Recombinant viruses are generated from the genome of viruses through genetic engineering. This genetic engineering often involves insertion of heterologous DNA including, but not limited to, DNA encoding a therapeutic product into the adenovirus genome. It is to be understood, however, that the term “recombinant virus” is also meant to include virus from which parts of the virus genome have been removed without insertion of heterologous DNA. Another example of a recombinant virus is a chimeric virus containing parts of the genomes of different viruses or of different types of the same virus, such as, e.g., different serotype viruses or viruses with different host animal species specificities.

As used herein, two types of recombinant viruses are discriminated, i.e., replication-deficient virus and replication-competent virus.

In a first type of replication-competent adenovirus, no parts of the adenovirus genome have been removed or parts of the adenovirus genome that are removed do not include parts that are essential for at least one step of the adenovirus infectious life cycle. This type of recombinant adenovirus is, therefore, also defined as a genuine replication-competent adenovirus that has a capacity to replicate in cells like the parental unmodified adenovirus does. In general, the replication of adenoviruses is restricted to cells of a particular animal species or group of animal species. For example, recombinant adenoviruses derived from human adenoviruses can only transverse a complete life cycle in human cells, with very inefficient replication occurring at a high dose in cells of some other species.

A second type of replication-competent adenovirus is the so-called conditionally replicating adenovirus (CRAd). In CRAds, one or more parts of the adenovirus genome are removed, including parts that are essential for at least one step of the adenovirus infectious life cycle under certain physiological conditions (herein also referred to as “first conditions”) but not under certain other physiological conditions (herein also referred to as “second conditions”). The first and second conditions could, e.g., be dictated by the physiological conditions that exist in a particular type of cells (herein also referred to as “first cells”), but not in another type of cells (herein also referred to as “second cells”). Such a first type of cell is, for instance, a cell derived from a particular type of tissue, where the cell contains a protein that is not or much less present in cells from other tissues (second type of cells). An example of a second type of cell is a cell that has lost proper cell growth control, such as, for example, a cancer cell, where the cell either lacks a protein that is present in cells that have not lost proper cell growth control or where the cell has gained expression (or over-expression) of a protein that is not or much less present in cells that have not lost proper cell growth control. Another example of the second conditions is the conditions that exist in a particular stage of the cell cycle or in a particular developmental stage of the cell, where a certain protein is expressed specifically. Thus, CRAds can be designed such that replication thereof is enabled in particular cells, such as cancer cells or a particular type of cancer cells, whereas in normal cells, replication of CRAds is not possible. This is known in the art and reviewed, e.g., by Heise and Kim, *J. Clin. Invest.* 105(2000):847-851; Alemany et al., *Nat. Biotech.* 18(2000):723-727; Gomez-Navarro and Curiel, *Lancet Oncol.* 1(2000):148-158).

In a third type of replication-competent adenovirus, parts of the genome are removed that include the function to be replicated in the target cell, but the function is complemented by inserting one or more functional expression cassettes for heterologous proteins that provide the function in the recombinant adenovirus genome. This type of recombinant adenovirus is referred to herein as a heterologously trans-complemented adenovirus and, therefore, is to be regarded as replication-competent according to the definition presented herein.

The adenovirus replication process constitutes the following steps: (1) infection of the host cell by binding of the adenovirus particle to the cell surface, internalization and transport towards the cell nucleus, and import of the adenovirus DNA genome into the cell nucleus, (2) expression of adenovirus proteins encoded by the early regions in the adenovirus genome, (3) replication of the adenovirus genome, which marks the transition of the early replication phase to the late replication phase, (4) expression of adenovirus proteins encoded by the late regions in the adenovirus genome, (5) assembly of progeny adenovirus particles and inclusion of progeny adenovirus genomes into these particles, and (6) induction of cell death, leading to release of adenovirus progeny from the cell.

During their life cycle, adenoviruses modulate cell-death pathways. In different cell lines, p53-dependent, as well as p53-independent, apoptosis has been documented after adenovirus infection (Teodoro and Branton, *J. Virol.* 71(1997): 1739-1746, and references therein). During the early replication phase, cell death is suppressed to prevent premature cell death, thereby allowing the adenovirus to complete its life cycle in the cell. In contrast, at late stages of infection, cell death and lysis are promoted to release the virus progeny from the cell.

The production of recombinant adenoviruses usually starts with genetic engineering of at least a part of the adenovirus genome by standard molecular biology techniques known in the art. Next, the adenoviral genome, comprised of one or more (in this case overlapping) constructs, is introduced into cells that allow replication of the recombinant adenovirus by DNA transfer methods known in the art. After the recombinant adenovirus has started to replicate in cells into which the recombinant adenovirus genome has been introduced, the recombinant adenovirus can spread to other cells in the culture.

The recombinant adenovirus can also be isolated from the culture medium or from lysates of the cells in which the recombinant adenovirus is replicating. The isolated recombinant adenovirus can then be used to re-infect new cells to further propagate and expand the recombinant adenovirus. In addition, the recombinant adenovirus can be administered to an animal or human body to infect cells in vivo. This administration can be done via several routes including, but not limited to, direct injection into a tissue, oral administration, injection into the blood circulation, inhalation, injection into a body cavity, and application to the surface of a certain body area. Following infection of the cells in vivo, the recombinant adenovirus can replicate and spread to other cells in vivo, provided that the infected cells support replication of the recombinant adenovirus.

Replication-competent adenoviruses will replicate in many different cells in an animal body, provided that they are derived from adenoviruses with the correct species tropism and that the cells express surface receptors for the adenoviruses. Specific cell surface recognition by recombinant adenoviruses, including replication-competent adenoviruses, can be changed. by pseudotyping or targeting (Krasnykh et al., *Mol. Ther.* 1(2000):391-405; Havenga et al., *J. Virol.* 76(2002):4612-4620; van Beusechem et al., *Gene Ther.* 10(2003):1982-1991). CRAds will only replicate in cells in which the particular conditions exist that are required for replication of the CRAd. CRAds are designed to meet the specific requirements for replication in a chosen (first) type of cell and not in other (second) types of cells. This property makes CRAds particularly useful for several embodiments of the present invention where the intent is to treat a disease by specific lytic replication of the recombinant adenovirus, described herein, in diseased cells in an animal or human body, resulting in specific removal of the diseased cells from the body.

Replication-competent viruses, in particular, adenoviruses, are finding increasing utility for the treatment of cancer and other diseases involving inappropriate cell survival. In particular, CRAds have been developed to selectively replicate in and kill cancer cells. Such cancer-specific CRAds represent a novel and very promising class of anticancer agents (reviewed by Heise and Kirn, supra; Alemany et al., supra; Gomez-Navarro and Curiel, supra). The tumor-selective replication of this type of CRAds is achieved through either of two alternative strategies.

In the first strategy, the expression of an essential early adenovirus gene is controlled by a tumor-specific promoter (e.g., Rodriguez et al., *Cancer Res.* 57(1997):2559-2563; Hallenbeck et al., *Hum. Gene Ther.* 10(1999):1721-1733; Tsukuda et al., *Cancer Res.* 62(2002):3438-3447; Huang et al., *Gene Ther.* 10(2003):1241-1247; Cuevas et al., *Cancer Res.* 63(2003):6877-6884).

The second strategy involves the introduction of mutations in viral genes to abrogate the interaction of the encoded RNA or protein products with cellular proteins necessary to complete the viral life cycle in normal cells, but not in tumor cells (e.g., Bischoff et al., *Science* 274(1996):373-376; Fueyo et al., *Oncogene* 19(2000):2-12; Heise et al., *Clin. Cancer Res.* 6(2000):4908-4914; Shen et al., *J. Virol.* 75(2001:4297-4307; Cascallo et al., *Cancer Res.* 63(2003):5544-5550).

During their replication in tumor cells, CRAds destroy cancer cells by inducing lysis, a process that is further referred to as "oncolysis." The release of viral progeny from lysed cancer cells offers the potential to amplify CRAds in situ and to achieve lateral spread to neighboring cells in a solid tumor, thus expanding the oncolytic effect. The restriction of CRAd replication to cancer or hyperproliferative cells dictates the safety of the agent, by preventing lysis of normal tissue cells. Currently, CRAd-based cancer treatments are already being evaluated in clinical trials (e.g., Nemunaitis et al., *Cancer Res.* 60(2000):6359-6366; Khuri et al., *Nature Med.* 6(2000):879-885; Habib et al., *Hum. Gene Ther.* 12(2001):219-226).

However, despite very encouraging results from in vitro and animal studies, the anti-cancer efficacy of CRAds as a single agent in humans has been limited (Kim et al., *Nature Med.* 4(1998):1341-1342; Ganly et al., *Clin. Cancer Res.* 6(2000):798-806; Nemunaitis et al., *Cancer Res.* 60(2000): 6359-6366; Mulvihill et al., *Gene Therapy* 8(2001):308-315). Thus, there is a clear need in the field of cancer treatment to increase the potency of replication-competent adenoviruses as oncolytic agents. This could be achieved by enhancing their replication and lysis capacities.

Several approaches aimed at improving the replication and lysis capacities of replication-competent adenoviruses, or at preventing loss of these functions from the wild-type adenovirus, have been taken. It has been shown that it is better to retain the adenovirus E3 region in a replication-competent adenovirus (Yu et al., *Cancer Res.* 60(2000):4200-4203) or, in case most of the E3 region is deleted, to at least retain the gene encoding the E3-11.6 kDa protein (Tollefson et al., *J. Virol.* 70(1996):2296-2306; Doronin et al., *J. Virol.* 74(2000): 6147-6155). In addition, replication and cell lysis of replication-competent adenoviruses have been improved by incorporation of cytotoxic genes (Zhang et al., *Proc. Natl. Acad. Sci. USA* 93(1996):4513-4518; Freytag et al., *Hum. Gene Ther.* 9(1998):1323-1333; Wildner et al., *Gene Ther.* 6(1999): 57-62). It was also shown that replication-competent adenoviruses are more potent in killing cancer cells when they are deleted of the gene encoding the anti-apoptotic E1B-19 kDa protein (Martin Duque et al., *Cancer Gene Ther.* 6(1999): 554-563; Sauthoff et al., *Hum. Gene Ther.* 11(2000):379-388).

Recently, we found that oncolysis and release of adenovirus progeny from infected cancer cells can be accelerated by restoring p53 functions in the cancer cells (van Beusechem et al., *Cancer Res.* 62(2002):6165-6171; PCT International Patent Application WO 03/057892, incorporated by reference herein). Restoration of p53 functions is done by expressing in the cancer cells a restoring factor, i.e., a functional factor of the p53-dependent apoptosis pathway, the function whereof is not or insufficiently expressed in the cancer cells, wherein the restoring factor preferably comprises a protein (WO 03/057892). Hence, the restoring factor is an essential positive component of the p53-dependent apoptosis pathway.

Cancer cells and cell lines are the result of neoplastic transformation. The genetic events underlying neoplastic transformation include activation of proto-oncogenes and inactivation of tumor-suppressor genes. A major player in this respect is the gene encoding the tumor-suppressor protein p53.

The p53 protein is the central coordinator of damage-induced cell-cycle checkpoint control. In a perturbed cell, p53 can induce growth arrest and cell death. p53 exerts these effects by functioning as a specific transcription factor that controls the expression of a large panel of genes involved in growth control, DNA repair, cell-cycle arrest, apoptosis promotion, redox regulation, nitric oxide production, and protein degradation (Polyak et al., *Nature* 389(1997):237-238; El-Deiry, *Sem. Cancer. Biol.* 8(1998):345-357; Yu et al., *Proc. Natl. Acad. Sci. USA* 96(1999):14517-14522; Hupp et al., *Biochem. J.* 352(2000):1-17; and references therein).

The induction of cell death by p53 is mediated, at least in part, by activation of pro-apoptotic death genes of the bcl-2 family, such as bax, bak, bad, bid, bik, bim, bok, blk, hrk, puma, noxa and bcl-x$_s$ (Miyashita and Reed, *Cell* 80(1995): 293-299; Han et al., *Genes Dev.* 10(1996):461-477; Zoernig et al., *Biochim. Biophys. Acta* 1551(2001):F1-F37). On the other hand, anti-apoptotic members of the bcl-2 family, such as bcl-2 itself and bcl-x$_L$, bcl-w, bfl-1, brag-1 and mcl-1 inhibit p53-dependent cell death (Zoernig et al., supra). The anti-apoptotic protein Bax Inhibitor-1 (BI-1) suppresses apoptosis through interacting with bcl-2 and bcl-x$_L$, (Xu and Reed, *Mol. Cell* 1 (1998):337-346).

The immediate effector proteins of p53, as well as p53 itself, target mitochondria, thereby releasing cytochrome c into the cytosol to activate the caspase cascade via the initiator caspase-9/Apaf-1 complex (Juergensmeier et al., *Proc. Natl. Acad. Sci. USA* 95(1998):4997-5002; Fearnhead et al., *Proc. Natl. Acad. Sci. USA* 95(1998):13664-13669; Soengas et al., *Science* 284(1999):156-159; Marchenko et al., *J. Biol. Chem.* 275(2000):16202-16212). Negative regulators of the caspase cascade include, but are not limited to, members of the Inhibitor of Apoptosis Protein (IAP) family of proteins, such as cIAP1, cIAP2, cIAP3, XIAP and survivin (Zoemig et al., supra).

The loss of normal function of p53 is associated with resistance to programmed cell death, cell transformation in vitro and development of neoplasms in vivo. In approximately 50% of human cancers, the gene encoding p53 is non-functional through deletion or mutation (Levine et al., *Nature* 351(1991):453-456; Hollstein et al., *Science* 253(1991):49-53; Chang et al., *J. Clin. Oncol.* 13(1995): 1009-1022). In many of the other, 50% cancer cells that do express wild-type p53 protein, p53 function is still hampered by the action of a "p53 antagonist." A "p53 antagonist" is defined herein as a molecule capable of inhibiting p53 function. For example, loss of the tumor-suppressor protein p14ARF or overexpression of the MDM2 protein can lead to functional inactivation of p53 by binding to the MDM2 protein and subsequent degradation (Landers et al., *Oncogene* 9(1994):2745-2750; Florenes et al., *J. Nat. Cancer Inst.* 86(1994):1297-1302; Blaydes et al., *Oncogene* 14(1997): 1859-1868; Stott et al., *EMBO J.* 17(1998):5001-5014; Schmitt et al., *Genes Dev.* 19(1999):2670-2677). Other non-limiting examples of molecules that promote p53 degradation include Pirh2 (Leng et al., *Cell* 112(2003):779-791), COP1 (Dornan et al., *Nature* 429(2004):86-92) and Bruce (Ren et al., *Proc. Natl. Acad. Sci. USA* 102(2005):565-570).

Another example is functional inactivation of p53 as a result of the antagonizing binding of human papilloma virus (HPV) E6 protein in cervical carcinomas (Scheffner et al., *Cell* 63(1990):1129-1136) or of herpesvirus-8 latency-associated nuclear antigen (LANA) in Kaposi's sarcoma (Friborg et al., *Nature* 402(1999):889-894). Yet another example is functional inactivation of p53 as a result of cytoplasmic retention through binding of p53 to Parc (Nikolaev et al., *Cell* 112(2003):29-40) or to mot-2/mtbsp70/GRP75/mortalin (Wadhwa et al., *Exp. Cell Res.* 274(2002):246-253).

Furthermore, some molecules can indirectly reduce the amount of functional p53 in a cell and are, therefore, also considered herein as p53 antagonists, although they are not considered members of the p53 pathway. For example, elevated expression of polo-like kinase-1 (plk-1) decreases p53 stability (Liu and Erikson, *Proc. Natl. Acad. Sci. USA* 100(2003):5789-5794). In addition, even if the p53 function itself is intact, p53-dependent cell death can be hampered due to overexpression of anti-apoptotic proteins acting on the p53 pathway down-stream from p53, such as the anti-apoptotic bcl-2 and IAP family members and BI-1. Another example is p73DeltaN, which binds to p53-responsive promoters competing with p53, thereby antagonizing p53-dependent cell death (Kartasheva et al., *Oncogene* 21(2002):4715-4727). For the purpose of the invention, the anti-apoptotic proteins acting on the p53 pathway down-stream from p53 are referred to as "p53 pathway inhibitors." Thus, in many, if not all, cancers in vivo and cancer-derived or immortalized cell lines in vitro, p53-dependent cell death is hampered as a result of one or more lesions in the p53 pathway.

Loss of p53 function has also been documented in other diseases involving inappropriate cell survival, such as, for example, rheumatoid arthritis (Firestein et al., *J. Clin. Invest.* 96(1995):1631-1638; Firestein et al., *Am. J. Pathol.* 149 (1996):2143-2151; Firestein et al., *Proc. Natl. Acad. Sci. USA* 94(1997):10895-10900) and vascular smooth muscle cell hyperplasia (Speir et al., *Science* 265(1994):391-394; Kovacs et al., *Am J. Pathol.* 149(1996):1531-1539).

Other molecules involved in regulation of programmed cell death include, but are not limited to, members of the death effector domain protein family (reviewed by Tibbetts et al., *Nat. Immunol.* 4(2003):404-409). It is to be understood that many anti-apoptotic proteins known to be important in the regulation of programmed cell death or cancer cell maintenance do not act on the p53 pathway. They are, therefore, not considered members of the p53 pathway. For example, inhibition of cyclin E, DNA replication initiation proteins, fatty acid synthase, or PAX2 caused apoptosis in cancer cells (Li et al., *Cancer Res.* 63(2003):3593-3597; Feng et al., *Cancer Res.* 63(2003):7356-7364; de Schrijver et al., *Cancer Res.* 63(2003):3799-3804; Muratovska et al., *Oncogene* 22(2003): 6045-6053). Therefore, in all of these targets, the inhibition whereof leads to apoptosis and that are not members of the p53 pathway, are considered anti-apoptotic proteins for the purpose of the invention. Many genes known to be important in the regulation of programmed cell death or cancer cell maintenance have been shown to be targets for anti-cancer therapy (reviewed by Jansen and Zangemeister-Wittke, *Lancet Oncol.* 3(2002):672-683). Several methods have been used successfully to selectively suppress these targets, including expression of dominant-negative proteins, introduction of small inhibitor molecules, RNA antisense expression and RNA interference. The present invention makes use of RNA interference.

RNA interference (RNAi) is a conserved cellular surveillance system that recognizes double-stranded RNA (dsRNA) and activates a sequence-specific degradation of RNA species homologous to the dsRNA (Hannon, *Nature* 418(2002):244-251). In addition, RNAi can cause transcriptional gene silencing by RNA-directed promoter DNA methylation and/or histone methylation (Kawasaki and Taira, *Nature* 431(2004): 211-217; Morris et al., *Science* 305(2004):1289-1292). Furthermore, in some species, RNAi has been implicated in programmed DNA elimination and meiotic silencing (reviewed by Matzke and Birchler, *Nature Rev. Genet.* 6(2005): 24-35). The observation that dsRNA could elicit a potent and specific gene silencing effect was first made in experiments with *Caenorhabditis elegans* where dsRNA, a byproduct in the generation of antisense RNA, proved to be more effective than antisense RNA itself (Fire et al., *Nature* 391(1998):806-81 1). In retrospect, this observation offered an explanation for the phenomenon of post-transcriptional gene silencing frequently encountered in transgenic plants (Baulcombe, *Plant Mol. Biol.* 32(1996):79-88). After these initial reports, RNAi-related processes have been described in almost all eukaryotic organisms, including protozoa, flies, nematodes, insects, parasites, and mouse and human cell lines (reviewed in: Zamore, *Nat. Struct. Biol.*, 8(2001):746-750; Hannon, *Nature* 418(2002):244-251; Agrawal et al., *Microbiol. Mol.*

Biol. Rev. 67(2003):657-685). By now, RNA interference is the most widely used method to specifically down-regulate genes for functional studies.

The molecular mechanism of RNAi involves the recognition and cleavage of dsRNA into small interfering RNAs (siRNAs) by the RNase III enzymes Dicer and Drosha (Carmell and Hannon, Nat. Struct. Biol. 11(2004):214-218), the incorporation of the siRNAs in a multiprotein complex called RISC (RNA-induced silencing complex), and the degradation of homologous RNA(Caudy et al., Nature 425(2003): 411-414). The siRNAs perform an essential role in guiding RISC to the target mRNA. siRNAs consist of double-stranded 21 to 23 nucleotide RNA duplexes carrying two nucleotide 3'-OH overhangs that determine, in part, the efficacy of gene silencing (Elbashir et al., Genes Dev. 15(2001):188-200).

During the incorporation of the siRNA into the RISC complex, the siRNA is unwound and only one strand is assembled into the active RISC complex. This process is asymmetric in nature and RISC preferentially accepts the strand of the siRNA that presents the less stable 5' end (Khvorova et al., Cell 115(2003):209-216; Schwarz et al., Cell 115(2003):199-208). This has important ramifications in the selection of siRNA sequences because only siRNAs from which the antisense strand (with regard to the targeted mRNA) is assembled into RISC will be effective. Guidelines have been proposed for the selection of highly effective siRNA sequences based on the free energy profile of the siRNA sequences (Khvorova et al., Cell 115(2003):209-216; Schwarz et al., Cell 115(2003):199-208; Reynolds et al., Nat. Biotechnol. 22(2004):326-330; Ui-Tei et al., Nucleic Acids Res. 32(2004):936-948).

Application of dsRNA to silence expression of genes in mammalian cells lagged behind due to the occurrence of a general response triggered by dsRNA molecules larger than 30 basepairs. This response is mediated by dsRNA-activated protein kinase (PKR) and 2', 5' OligoA-synthetase/RNAseL and results in a shut down of translation followed by apoptosis (Kumar and Carmichael, Microbiol. Mol. Biol. Rev. 62(1998):1415-1434; Gil and Esteban, Apoptosis 5(2000): 107-114). Therefore, initially, application of RNAi by long dsRNA was confined to mammalian cells that lack the PKR response: i.e., embryonic cells (Billy et al., Proc. Natl. Acad. Sci. USA 98(2001):14428-14433; Svoboda et al., Development 127(2000):4147-4156). In a breakthrough experiment, Elbashir and coworkers showed that chemically synthesized siRNAs, resembling the siRNAs produced by Dicer and Drosha, induced gene-specific silencing in cultured mammalian cells without triggering the PKR response (Elbashir et al., Nature 411(2001):188-200). Synthesized siRNAs are now widely used as a tool to study the function of individual genes offering a convenient and rapid method to silence genes (McManus and Sharp, Nat. Rev. Genet. 3(2002):737-747). However, the transient nature of the silencing effect and the difficulty of delivering synthetic siRNAs in vivo restrict the utility of this approach.

A further means of generating siRNAs is to express small RNA molecules inside the cell, either by co-expression of sense and antisense RNAs (Zheng et al., Proc. Natl. Acad. Sci. USA 101(2004):135-140; Miyagishi et al., Nat. Biotechnol. 20(2002):497-500; Lee et al., Nat. Biotechnol. 20(2002):500-505), or as a single transcript that forms a stem-loop structure. The latter RNA molecules are generally referred to as short hairpin RNAs (shRNAs) and typically consist of a 19 to 29 nucleotide stem containing complementary sense and antisense strands and a loop of varying size. shRNAs generated inside the cell are processed by Dicer to form siRNAs and are capable of inducing RNAi.

A variety of promoters have been used to drive the expression of shRNAs. RNA polymerase III promoters are especially suited because they have well-defined initiation sites and a termination site consisting of a stretch of at least four consecutive thymidine nucleotides. The RNA polymerase III (polIII) promoters H1, U6 and tRNA(Val) have been successfully used to express shRNAs (Brummelkamp et al., Science 296(2002):550-553; Paddison et al., Genes Dev. 16(2002) 948-958; Kawasaki and Taira, Nucleic Acids Res. 31 (2003): 700-707).

Recently, polIII-based drug-inducible shRNA expression cassettes have been developed that permit the conditional suppression of genes in mammalian cells (Wiznerowicz and Trono, J. Virol. 77(2003):8957-8961; Gupta et al., Proc. Natl. Acad. Sci. USA 101(2004):1927-1932). RNA polymerase II promoters (polII) are less suited to express functional shRNAs and initial attempts failed to induce silencing (Paddison et al., Genes Dev. 16(2002)948-958). However, successful use of the polII CMV promoter was reported by using a minimal CMV promoter and a modified polyA signal (Xia et al., Nat. Biotechnol. 20(2002):1006-1010) or by using ribozyme-mediated cleavage of the transcript (Kato and Taira, Oligonucleotides 13(2003):335-343; Shinagawa and Ishii, Genes Dev. 17(2003):1340-1345).

Reports that shRNAs expressed from.plasmids could trigger RNAi allowed the use of viral vectors. Retroviral or lentiviral delivery into mammalian cells leads to stable integration of the shRNA-expression cassette in the genome and long-term, sustained gene suppression and is frequently used (e.g., Brummelkamp et al., Science 296(2002):550-553; An et al., Hum. Gene Ther. 14(2003): 1207-1212).

Adenoviral vectors infect dividing and non-dividing cells but remain episomal. Non-replicating adenoviral vectors expressing shRNAs have been shown to induce silencing of target genes in vitro and in vivo (Xia et al., Nat. Biotechnol. 20(2002):1006-1010; Arts et al., Genome Res. 13(2003): 2325-2332; Shen et al., FEBS Lett. 539(2003):111-114; Zhao et al., Gene 316(2003):137-141; WO 2004/013355). So far, RNAi with viral vectors has only been done using replication-deficient viral vectors. For clarity, it is repeated here that the present invention relates only to replication-competent virus. It has not been suggested before to employ RNAi in the context of a replication-competent virus because this is not obvious. RNAi has been recognized as a cellular defense mechanism against viral infection and this had led many viruses to evolve molecules that inhibit RNAi (Cullen, Nature Immunol. 3(200):597-599; Roth et al., Virus Res. 102(2004): 97-108). Therefore, prior to the present invention, there was reason to assume that the process of RNAi would be hampered in cells in which a virus is replicating. The results disclosed herein, which could not be predicted from prior literature, demonstrate that RNAi can be successfully employed in the context of a replication-competent virus.

RNA interference in mammalian cells is now widely used to analyze the function of individual genes. Numerous genes have been successfully silenced in mammalian cells, either by transfection of chemically synthesized siRNA or by expression of shRNAs. Classes of genes targeted include genes involved in signal transduction, cell-cycle regulation, development, cell death, etc. (Milhavet et al., Pharmacol. Rev. 55(2003):629-648). Systematic studies for delineating gene function on a genome scale are feasible when large libraries targeting human genes are available. Large libraries of chemically synthesized siRNAs are already commercially available (from Dharmacon and Qiagen), which cause strong, but transient, inhibition of gene expression.

By contrast, vector-expressed shRNAs can suppress gene expression over prolonged periods. Two research groups (Berns et al., *Nature* 428(2004):431-437; Paddison et al., *Nature* 428(2004):427-431) independently constructed and reported on an shRNA-based library covering 7,914 and 9,610 human genes, respectively. Both libraries use polIII promoters and a retroviral vector based on self-inactivating murine-stem-cell virus. These libraries will aid in identifying gene function in mammalian cells using high-throughput genetic screens. Berns et al. (supra) already used their library to identify new components of the p53 pathway by screening for inhibition of cell senescence. It is expected that synthetic lethal high-throughput screenings will be performed to evaluate shRNAs for their ability to kill engineered tumorigenic cells but not their isogenic normal cell counterparts (Brummelkamp and Bernards, *Nat. Rev. Cancer* 3(2003):781-789). Thus, identification of selective anti-cancer shRNAs is foreseen.

BRIEF SUMMARY OF THE INVENTION

In many instances, it is preferred that a replication-competent adenovirus undergo a rapid life cycle in a host cell. When a replication-competent adenovirus is produced or when a replication-competent adenovirus is used as a vector to produce a protein in cells, a rapid adenovirus life cycle speeds up the production process. For example, when a replication-competent adenovirus is used as a means to kill a population of cells, a rapid life cycle will add to the efficacy of the process. A rapid life cycle is of particular importance for the use of a replication-competent adenovirus in vivo. Adenoviruses induce potent immune responses in the body of animals that inactivate the adenoviruses. This limits the duration of in vivo replication of an administered replication-competent adenovirus. A faster life cycle will thus allow more cycles of progeny virus production within the time span between administration and inactivation of the replication-competent adenovirus.

Described herein are recombinant viruses that silence expression of certain genes in certain cells, which causes the viruses to more effectively replicate in and lyse the cells. Provided are more efficient means to eradicate certain populations of cells. Furthermore provided are methods and means to identify target genes, the silencing whereof causes viruses to more effectively replicate in and lyse cells in which they replicate. Also provided are recombinant viruses that silence expression of the identified target genes in the cells, which causes the viruses to more effectively replicate in and lyse the cells. The invention finds useful applications in the areas of viral vector production, therapeutic target identification, and medical treatments based on inhibition of protein expression and removal of certain cells from a body, such as, for example, cancer cells.

A situation where a rapid life cycle of a replication-competent adenovirus is of particular importance in vivo is in the context of the treatment of a disease involving inappropriate cell survival. A paradigm example of such a disease is cancer. The anticancer potency of a replication-competent adenovirus that is administered to a tumor in vivo depends on (1) the efficiency at which the virus disseminates throughout the tumor by producing progeny that can infect neighboring tumor cells, and (2) the efficiency at which the virus kills tumor cells via replication and lysis of the cells. Thus, a rapid life cycle will result in a faster oncolysis, more cycles of new virus production per time, infection of more tumor cells in time, and, consequently, more effective tumor destruction.

Therefore, provided are replication-competent adenoviruses that have a short replication time in a host cell. "Replication time" is understood to mean the time between entry of the replication-competent adenovirus into the cell and the release of progeny of the replication-competent adenovirus from the cell.

Also provided are replication-competent adenoviruses that have a fast lytic capacity. A fast lytic capacity is understood to mean a short time required to lyse a host cell after entry of the replication-competent adenovirus into the host cell.

The short replication time and/or fast lytic capacity of the replication-competent adenovirus is brought about by silencing the expression of one or more target genes in the host cell through RNA interference. It is thus to be clearly understood that the present invention utilizes RNA interference to provide the replication-competent adenovirus with the short replication time and/or fast lytic capacity.

In embodiments of the invention, RNA interference is induced by one or more silencing factors that are expressed from the genome of the replication-competent adenovirus, where it is further preferred that the silencing factors are shRNA molecules. In another embodiment, the silencing factors consist of double-stranded RNA molecules that are formed in the cell from two RNA molecules expressed from the genome of the replication-competent adenovirus.

In other embodiments, the host cell in which the replication-competent adenoviruses have a short replication time and/or a fast lytic capacity is a cell expressing one or more adenovirus inhibitory factors. In one embodiment, the host cell is a cell with a defect in a cell death pathway. In another embodiment of the invention, the host cell is hampered in the p53-dependent cell death pathway. That cell is preferably a human cell. Non-limiting examples of host cells useful herein are cancer or tumor cells, arthritic cells and hyperproliferative vascular smooth muscle cells.

It is to be understood that a "defect in a cell death pathway" includes the inability of a cell to respond to a loss of cell-cycle checkpoint control, to DNA damage and/or to oncogene expression by executing programmed cell death. The defect in a cell death pathway causes "inappropriate cell survival."

In certain embodiments, the host cell is a cell that is being cultured in vitro. In another embodiment, the host cell is a cell in an animal body where it is preferred that the animal body is a human body.

In one embodiment, the fast lytic capacity is the result of restoration of the defect in a cell death pathway. In a further embodiment of the invention, the restoration is in the p53-dependent cell death pathway.

In an embodiment, the replication-competent adenovirus expressing one or more silencing factors from its genome described herein furthermore expresses a functional factor of the p53-dependent apoptosis pathway described herein disclosed in WO 03/057892, incorporated by reference herein. This embodiment thus provides the combined effect of restoring the p53-dependent apoptosis pathway by expressing the functional factor and of silencing one or more adenovirus inhibitory factors by the one or more silencing factors.

Thus, the replication-competent adenoviruses described herein are capable of replicating in a host cell and expressing one or more silencing factors. The silencing factors silence the expression of a host cell factor capable of inhibiting the short replication time and/or fast lytic capacity of replication-competent adenoviruses in the host cell. The host cell factor that inhibits the short replication time and/or fast lytic capacity of the replication-competent adenovirus is further referred to as an "adenovirus inhibitory factor." The character of the adenovirus inhibitory factor is not dictated in any way other than it being expressed in the host cell and being capable of inhibiting adenovirus replication or adenovirus-induced host cell lysis. Non-limiting examples of the adenovirus inhibitory factor are p53 antagonists and p53 pathway inhibitors. Further non-limiting examples of the adenovirus inhibitory factor are anti-apoptotic proteins that are not members of the p53 pathway. Other non-limiting examples of the adenovirus inhibitory factor are molecules that are identified by using a method to identify an adenovirus inhibitory factor described herein (infra). The amount of silencing brought about by one or more silencing factors should be sufficient to decrease the amount of adenovirus inhibitory factor to a level that allows the short replication time and/or fast lytic capacity of the replication-competent adenovirus of the invention in the cell.

In various embodiments, the replication-competent adenovirus expressing one or more silencing factors from its genome described herein furthermore comprises one or more modifications in its genome known in the art that change its tropism, i.e., target cell recognition specificity.

In another embodiment, the replication-competent adenovirus expressing one or more silencing factors from its genome described herein furthermore comprises one or more modifications in its genome known in the art that reduce its immunogenicity.

In yet another embodiment, the replication-competent adenovirus expressing one or more silencing factors from its genome described herein furthermore comprises one or more modifications in its genome known in the art that restrict its replication in a first type of cells but not in a second type of cells.

In yet another embodiment, the replication-competent adenovirus expressing one or more silencing factors from its genome also comprises one or more modifications in its genome known in the art that augment its replication and/or lytic capacity.

As outlined above, it is to be clearly understood that the terms "replication competent" and "being capable of replicating in a host cell" mean that the recombinant adenoviruses alone are capable of completing their infectious life cycle in the host cell with the aid of the endogenous machinery of the host cell, without a need to provide any functions encoded by any removed parts of the genome of the recombinant adenoviruses by other means, such as the provision thereof in the genome of the host cell. The recombinant adenovirus is a replication-competent adenovirus, preferably a conditionally replicating adenovirus or a heterologously trans-complemented adenovirus. The recombinant adenovirus is not a replication-deficient adenovirus.

The term "silencing factor" means an RNA molecule capable of decreasing expression of a target gene through the process of RNA interference. The RNA molecule preferably comprises a double-stranded portion, preferably having a length of at least 19 nucleotides (per strand). The double-stranded portion preferably has a length of less than 30 nucleotides, and the RNA molecule preferably comprises a short hairpin RNA as outlined above (shRNA), or comprises a double-stranded structure consisting of two different RNA molecules having complementary regions of preferably the above length. In the latter case, the RNA molecules can be transcribed from different promotors. The RNA molecules are preferably susceptible to the action (i.e., the recognition and cleavage of dsRNA) of the above-mentioned RNAse III enzymes, resulting in the above-discussed siRNAs. The term "target gene" is understood to indicate that the process of decreasing expression of the gene occurs with specificity.

Also provided are formulations comprising the replication-competent adenoviruses described herein that can be used to preserve the replication-competent adenoviruses and to administer the replication-competent adenoviruses to cells. In one variation, the formulations are used to administer the replication-competent adenoviruses to cells in vitro. In another variation, the formulations are used to administer the replication-competent adenoviruses to cells in vivo.

Also provided are methods to administer the formulations described herein to cells, leading to infection of the cells with the replication-competent adenoviruses of the invention. In one variation, the methods are used to administer the formulations to cells in vitro. In another variation, the methods are used to administer the formulations to cells in vivo.

Also provided are compositions of the replication-competent adenoviruses described herein and cells in which the replication-competent adenoviruses described herein induce accelerated cell lysis and/or a faster release of virus progeny, compared to replication-competent adenoviruses that are not expressing one or more silencing factors described herein. In a preferred embodiment, the cells are cancer cells and the cell lysis is oncolysis. In a further preferred embodiment, the cells are human cells.

In another embodiment, the invention provides compositions of the replication-competent adenoviruses described herein and tumors in which the replication-competent adenoviruses described herein induce accelerated cell lysis and/or a faster release of virus progeny, compared to replication-competent adenoviruses that are not expressing one or more silencing factors described herein. In this aspect of the invention, it is preferred that the accelerated cell lysis and/or a faster release of virus progeny results in an accelerated lateral spread by the replication-competent adenoviruses from infected cells to neighboring cells in the tumors, compared to replication-competent adenoviruses that are not expressing one or more silencing factors described herein, where it is furthermore preferred that the accelerated cell lysis, faster release of virus progeny and/or accelerated lateral spread lead to a more effective destruction or growth inhibition of the tumors. In a preferred embodiment, the tumors are growing in an animal body. In a further variation, the animal body is a human body.

The invention furthermore provides methods to construct the replication-competent adenoviruses described herein and to produce the formulations and compositions described herein.

The invention furthermore contemplates the use of the replication-competent adenoviruses, methods and formulations described herein for the treatment of a disease which involves inappropriate cell survival, where it is preferred that the disease is a disease in a human being. In a particular embodiment of the invention the disease is cancer.

The invention furthermore provides methods to identify adenovirus inhibitory factors that are expressed in cells. In certain embodiments, the cells are cells with a defect in a cell death pathway and the cells are human cells.

The invention furthermore provides methods to identify and to select silencing factors that are useful for being expressed from the genome of the replication-competent adenoviruses described herein.

Hereinafter, in several embodiments, a number of ways to provide the replication-competent adenoviruses, silencing factors, formulations, methods, compositions, and uses are given. It is to be clearly understood that the description is not meant to in any way limit the scope of the invention as was explained in general terms above. Skilled artisans will be able to transfer the teachings of the present invention to other replication-competent adenoviruses, silencing factors, formulations, methods, compositions, and uses that are not mentioned specifically herein without departing from the present invention.

It is also to be understood that the invention includes all combined uses of the replication-competent adenoviruses, silencing factors, formulations, methods and compositions of the invention, together with other methods and means to kill a population of cells including, but not limited to, irradiation, introduction of genes encoding pro-apoptotic proteins, toxic proteins, such as, for example, toxins or prodrug converting enzymes, and administration of chemical compounds, antibodies, receptor antagonists, and the like.

The definitions of the terms used in the invention specification and claims are deemed either to be sufficiently defined herein or otherwise being clearly understood in the art. Further, any nucleic acid or amino acid sequence of factors/proteins described herein are known sequences, wherein reference is made to commonly available sequence databanks, such as the databanks of EMBL, Heidelberg, Germany, and GENBANK, both herein incorporated by reference.

DETAILED DESCRIPTION OF THE INVENTION

Figure 1A:
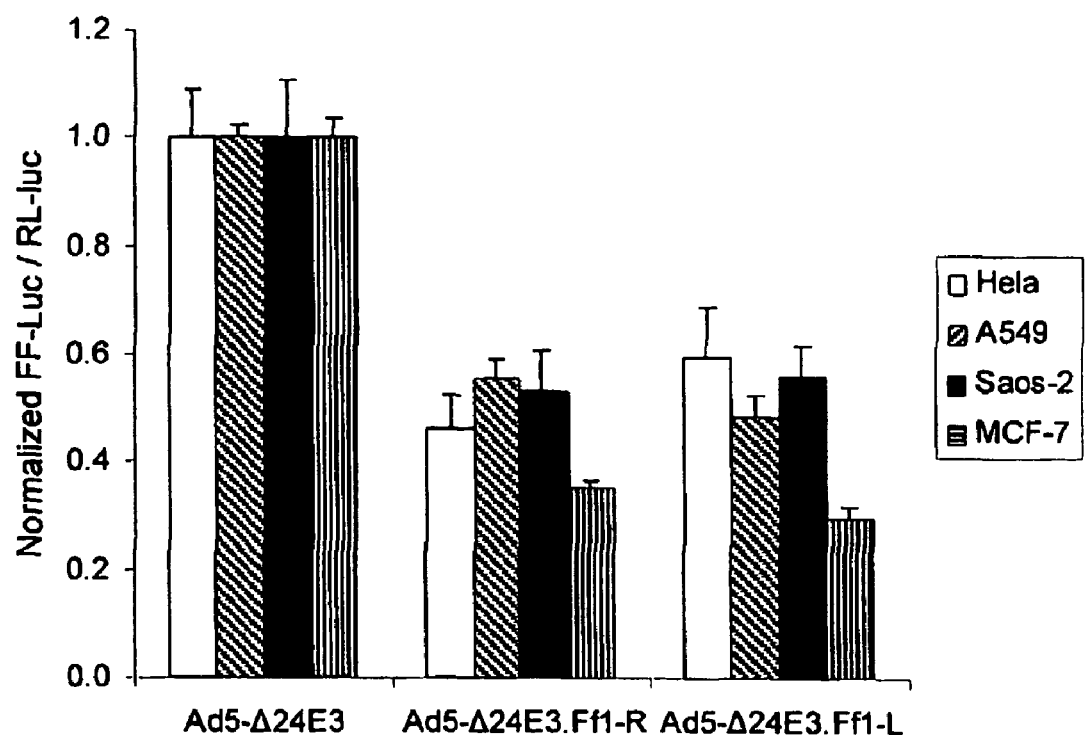
FIG. 1A. Conditionally replicating adenoviruses encoding shRNAs silence the expression of a target gene. CRAd-shRNA induced silencing of firefly luciferase in four human cell lines. Cells were infected with the indicated CRAds immediately followed by a transfection with the reporter plasmid phAR-FF-RL and silencing was analyzed 30 hours after infection. Ratios of firefly luciferase to Renilla luciferase activity were normalized to the ratio obtained after infection with the Ad5-Δ24E3 control virus. Data shown are the mean results+SD of a representative experiment performed in triplicate.

The invention and embodiments appear from the appended claims.

The present invention relates only to replication-competent virus.

Herein, the recombinant virus is exemplified by adenovirus. The term "adenovirus" can, therefore, be replaced by any suitable virus known in the art that is capable of infecting and lysing target cells. Non-limiting examples of other suitable viruses are herpes simplex viruses and vaccinia viruses. It is furthermore to be understood that in other terms defined herein that also contain the term "adenovirus," such as, e.g., "adenovirus inhibitory factor," the term "adenovirus" can be replaced by any suitable virus known in the art that is capable of infecting and lysing target cells.

"Replication-competent adenovirus" is defined herein in that the virus comprises, as part of its genome, the function to be replicated in the target cell, wherein replication is solely dependent on the replication functions provided by the virus, in combination with the endogenous cellular machinery of the target cells. The genome of the target cells is, therefore, free of any exogenous sequences encoding factors that are necessary for viral replication. These factors are provided by the genome of the replication-competent virus.

The term "exogenous" means in this respect that the cellular machinery (including the coding sequences therefor) necessary for virus replication is the naturally present machinery, e.g., not introduced in the cells by manipulation techniques by man. The latter are defined as "exogenous." The term "function to be replicated" includes the factors, such as proteins, encoded by the virus necessary for replication of the virus in the target cells (herein also referred to as viral replication factors). The factors may be endogenous for the virus, but may also be functional analogues encoded by the viral genome, e.g., in cases where the gene encoding the endogenous viral factor is deleted from the viral genome. It is important to note that these factors are encoded by the viral genome and are not to be complemented by exogenous factors encoded in target cells. Thus, viruses, of which the replication is dependent on one or more replication functions, being deleted from the virus but introduced in the target cell are defined to be replication-deficient and are, therefore, not part of the present invention. The invention as claimed relates to replication-competent viruses, i.e., wherein the viral genes encoding viral replication factors essential for regulation of virus replication in the target cells are present on the viral genome.

In one embodiment, the present invention provides a replication-competent adenovirus capable of replicating in a host cell, characterized in that the virus comprises at least one DNA sequence coding for a silencing factor, in particular a short hairpin RNA, capable of reducing expression of a target gene in the host cell, the DNA sequence being functionally linked to regulatory DNA sequences in such a manner that the silencing factor is expressed in the host cell into which the replication-competent adenovirus is introduced.

In a second embodiment, the present invention provides a replication-competent adenovirus capable of replicating in a host cell, characterized in that the virus comprises at least one DNA sequence coding for a silencing factor, in particular a short hairpin RNA, capable of reducing expression of an adenovirus inhibitory factor in the host cell, the DNA sequence being functionally linked to regulatory DNA sequences in such a manner that the silencing factor is expressed in the host cell into which the replication-competent adenovirus is introduced.

In certain embodiments, a replication-competent adenovirus is provided that comprises more than one DNA sequence coding for a silencing factor capable of reducing expression of a target gene in the host cell functionally linked to regulatory DNA sequences in such a manner that the silencing factor is expressed in a cell into which the replication-competent adenovirus is introduced. In one variation, at least two DNA sequences of more than one DNA sequence each encode for a different silencing factor capable of reducing expression of a different target gene. This embodiment is used to silence expression of more than one target gene in the host cell. In another variation, at least two DNA sequences of more than one DNA sequence each encode for a different silencing factor capable of reducing expression of the same target gene. This embodiment is used to more effectively silence expression of the target gene in the host cell.

In another embodiment, a replication-competent adenovirus is provided that comprises at least one DNA sequence coding for a silencing factor capable of reducing expression of a target gene in the host cell, the DNA sequence being functionally linked to regulatory DNA sequences in such a manner that the silencing factor is expressed in the host cell into which the replication-competent adenovirus is introduced, and furthermore comprises at least one open reading frame for a restoring factor capable of restoring the p53-dependent apoptosis pathway in the host cell according to WO 03/057892, the open reading frame being functionally linked to regulatory DNA sequences in such a manner that the restoring factor is expressed in the host cell into which the recombinant adenovirus is introduced.

Useful silencing factors that are to be expressed from the genome of the replication-competent adenoviruses of the invention in host cells in which the replication-competent adenoviruses are replicating form double-stranded RNA molecules that are processed by Dicer in the host cells to form siRNAs that are capable of inducing RNAi in the host cells.

The virus can be replicated in the host cell in several ways as discussed above. The skilled person will be aware of suitable replication strategies useful for the practice of the invention.

The recombinant adenovirus described herein is a replication-competent adenovirus, such as (1) a genuine replication-competent adenovirus (2) a conditionally replicating adenovirus, or (3) a heterologously trans-complemented adenovirus, or (4) a two-component replication-competent, heterologously trans-complemented, or conditionally replicating adenovirus consisting of, as a first component, a recombinant adenovirus that comprises at least one DNA sequence coding for a silencing factor capable of reducing expression of a target gene in the host cell, the DNA sequence being functionally linked to regulatory DNA sequences in such a manner that the silencing factor is expressed in the host cell into which the recombinant adenovirus is introduced and, as a second component, a replication-competent, heterologously trans-complemented, or conditionally replicating adenovirus, where a single-component replication-competent adenovirus according to possibilities 1, 2 or 3 is preferred.

Non-limiting examples of conditionally replicating adenoviruses described herein are derived from adenoviruses with controlled expression of at least one essential early adenovirus gene by a tumor-specific promoter including, but not limited to, those described by Rodriguez et al. (*Cancer Res.* 57(1997):2559-2563), Hallenbeck et al. (*Hum. Gene Ther.* 10(1999):1721-1733), Tsukuda et al. (*Cancer Res.* 62(2002): 3438-3447), Huang et al. (*Gene Ther.* 10(2003):1241-1247) and Cuevas et al. (*Cancer Res.* 63(2003):6877-6884), or adenoviruses with mutations in viral genes to abrogate the interaction of the encoded proteins with cellular proteins necessary to complete the viral life cycle in normal cells, but not in tumor cells, including, but not limited to, those described by Heise et al. (*Nature Med.* 6(2000):1134-1139), Balague et al. (*J. Virol.* 75(2001):7602-7611), Howe et al. (*Mol. Ther.* 2(2000):485-494), Fueyo et al. (*Oncogene* 19(2000):2-12), Shen et al. (*J. Virol.* 75(2001):4297-4307) and Cascallo et al. (*Cancer Res.* 63(2003):5544-5550), or adenoviruses comprising both types of modifications. A non-limiting example of a heterologously trans-complemented adenovirus described herein is derived from a recombinant adenovirus with a functionally deleted E1 region that expresses the HPV E6 and E7 proteins (Steinwaerder et al., *Mol. Ther.* 4(2001):211-216).

In one embodiment, the replication-competent adenovirus described herein is characterized in that the silencing factor is capable of reducing expression of a p53 antagonist including, but not limited to, MDM2, Pirh2, COP1, Bruce, HPV-E6, Parc, mortalin and plk-1.

In another embodiment, the replication-competent adenovirus described herein is characterized in that the silencing factor is capable of reducing expression of a p53 pathway inhibitor including, but not limited to, BI-1, p73DeltaN and the anti-apoptotic bcl-2 and IAP family members (supra).

In another embodiment, the replication-competent adenovirus described herein is characterized in that the silencing factor is capable of reducing expression of an adenovirus inhibitory factor, wherein the adenovirus inhibitory factor is characterized in that it delays replication of a replication-competent adenovirus lacking the silencing factor in a host cell or that it delays lysis of a host cell in which a replication-competent adenovirus lacking the silencing factor is replicating. It is to be clearly understood that in this embodiment of the invention, the character of the adenovirus inhibitory factor is not dictated in any way other than it being expressed in the host cell and being capable of inhibiting adenovirus replication or adenovirus-induced host cell lysis. "Being capable of inhibiting adenovirus replication or adenovirus-induced host cell lysis" means that in the presence of a sufficient amount of the adenovirus inhibitory factor in a host cell, 10% completion of the process of adenovirus replication or 50% completion of the process of adenovirus-induced host cell lysis is delayed in time by at least 10% compared to the otherwise identical situation in the absence of the adenovirus inhibitory factor, wherein it is preferred that the process is delayed by at least 20% and wherein it is more preferred that the process is delayed by at least 50%. In an embodiment, the adenovirus inhibitory factor is identified by a method described herein (infra).

Control sequences operably linked to the sequences encoding the silencing factor include promoters/enhancers and other expression regulation signals. These control sequences may be selected to be compatible with the host cell for which the expression vector is designed to be used in. The term promoter is well-known in the art and encompasses nucleic acid regions ranging in size and complexity from minimal promoters to promoters including upstream elements and enhancers. The promoter is typically selected from promoters that are functional in mammalian cells, although promoters functional in other eukaryotic cells may be used. The type of promoter is chosen to accomplish a useful expression profile for the silencing factor in the context of the replication-competent adenovirus. As described supra, RNA polymerase III promoters including, but not limited to, the U6, H1 and tRNA (Val) promoters are especially suitable for the invention, but other promoters are not excluded.

In certain embodiments, the DNA sequence coding for a silencing factor is functionally linked to one or more control sequences, i.e., regulatory DNA sequences, in such a manner that the silencing factor is expressed ubiquitously in a cell into which the replication-competent adenovirus is introduced. In another embodiment, the DNA sequence coding for a silencing factor is functionally linked to one or more control sequences, i.e., regulatory DNA sequences, in such a manner that the silencing factor is only expressed or is expressed at a higher level in a cell into which the replication-competent adenovirus is introduced under certain conditions that can be modulated by an external signal, where the term "external" means having its origin outside of the DNA fragment encompassing the DNA sequence coding for a silencing factor and the regulatory DNA sequences. In this aspect of the invention, the expression of the silencing factor is driven by a so-called regulatable or inducible promoter. In yet another embodiment, the DNA sequence coding for the silencing factor is functionally linked to regulatory DNA sequences in such a manner that the silencing factor is only expressed during the late phase of adenovirus replication in a cell into which the replication-competent adenovirus is introduced. In this aspect of the invention, it is preferred that expression of the silencing factor is driven by the adenovirus major late promoter (MLP), preferably the endogenous MLP.

The invention does not dictate the site of insertion of the DNA sequence coding for a silencing factor functionally linked to regulatory DNA sequences in the genome of the replication-competent adenovirus. Insertion may be at any location in the genome that does not inhibit replication of the replication-competent adenovirus in the cell into which the replication-competent adenovirus is introduced and where endogenous expression cassettes in the genome do not interfere with proper expression of the silencing factor. In non-limiting examples of the invention, insertion is a replacement of the adenovirus E3-region or insertion between the E4 promoter and the right-hand ITR. DNA constructs to generate recombinant adenoviruses with insertions in the E3-region are known in the art including, but not limited to, pBHG10 and pBHG11 (Bett et al., *Proc. Natl. Acad. Sci. USA* 91(1994):8802-8806), a DNA construct to generate recombinant adenoviruses with insertions between the E4 promoter and the right-hand ITR as described in Example 1, and insertions at other sites within the adenovirus genome can be made using standard molecular biology methods known in the art. In specific situations, it is preferred for proper expression of the open reading frame to shield the DNA sequence coding for a silencing factor functionally linked to regulatory DNA sequences from other regulatory DNA sequences present in the adenovirus genome by flanking the DNA sequence coding for a silencing factor functionally linked to regulatory DNA sequences by so-called insulator elements (Steinwaerder and Lieber, *Gene Therapy* 7(2000):556-567). In another embodiment, the DNA sequence coding for a silencing factor is inserted in place of an adenovirus gene, where it is preferred that the adenovirus gene is expressed during the late phase of adenovirus replication, and where it is further preferred that the adenovirus gene is functionally linked to the endogenous MLP.

It is to be understood that the invention also includes replication-competent adenoviruses described herein that additionally comprise one or more further modifications to change their characteristics including, but not limited to, a change of tropism through pseudotyping or targeting, such as, e.g., described by Krasnykh et al. (*Mol. Ther.* 1(2000):391-405), Suzuki et al. (*Clin. Cancer Res.* 7(20012):120-126), Van Beusechem et al. (*Gene Ther.* 10(2003):1982-1991) and Havenga et al. (*J. Virol.* 76(2002):4612-4620); expression of one or more transgenes, such as, e.g., a gene encoding a cytokine, a pro-apoptotic protein, an anti-angiogenic protein, a membrane fusogenic protein or a prodrug converting enzyme; or mutations that increase their replication potential, such as, e.g., retention of the E3 region (Suzuki et al., *Clin. Cancer Res.* 8(2002):3348-3359) or deletion of the E1B-19K gene (Sauthoff et al., *Hum. Gene Ther.* 11(2000):379-388), or their replication selectivity for a certain type of cells including, but not limited to, the modifications to make CRAds (supra), or that reduce their immunogenicity (i.e., their potency to induce an immune response when introduced into an animal body), such as, e.g., retention of the E3B region (Wang et al., *Nature Biotechnol.* 21(2003):1328-1335).

The replication-competent adenoviruses of the invention may be produced using molecular biology, virology and cell biology methods known in the art. A way to produce the replication-competent adenoviruses described herein is described in detail in the Examples section. It is to be understood, however, that this description is not meant in any way to limit the scope of the invention. Those skilled in the art will be able to derive the replication-competent adenoviruses of the invention using other methods or by using variations of the methods described herein.

In another embodiment, the invention provides methods to identify an adenovirus inhibitory factor that is a useful silencing target for the replication-competent adenoviruses of the invention, by comparing the replication time or the lytic capacity of a replication-competent adenovirus in a first type of host cells, in which the adenovirus inhibitory factor is silenced by a silencing factor, to the replication time or the lytic capacity of the replication-competent adenovirus in a second type of host cells, in which the adenovirus inhibitory factor is not silenced by a silencing factor, but that are otherwise identical to the first type of host cells, and by observing a shorter replication time or faster lytic capacity in the first type of host cells than in the second type of host cells.

Differences in replication time of replication-competent adenoviruses in two types of host cells can be measured, for example, by using a replication-competent adenovirus that expresses a marker gene, such as, e.g., the firefly luciferase gene, under regulation of the MLP. In this case, luciferase expression in the host cells depends on replication of the replication-competent adenovirus. Typically, luciferase expression by such a virus that is replicating in host cells will increase by more than 100-fold or even more than 1000-fold until replication is completed. A convenient measure for adenovirus replication rate in this case is the time required to reach 10% of the maximum value of luciferase activity. Luciferase activity is monitored in time by a method known in the art including, but not limited to, the Luciferase Chemiluminescent Assay System (Promega) or the ReportaLight Plus Kit (Cambrex), and a first type of host cells is identified in which the luciferase activity increases faster than in the second type of host cells. Faster in this case means in at least 10% less time, preferably at least 20% less time and more preferably at least 50% less time. The factor that is being silenced in the first type of host cells but not in the second type of host cells is then identified as being an adenovirus inhibitory factor.

Differences in lytic capacity can be measured, for example, by monitoring lysis of the host cells infected with a replication-competent adenovirus in time, using one of many methods known in the art including, but not limited to, the ToxiLight BioAssay (Cambrex), and identifying a first type of host cells that lyses faster than the second type of host cells. A convenient measure for adenovirus lytic capacity in this case is the time required to lyse 50% of the infected cells, i.e., the time required to reach 50% of the maximum value of the marker compound measured in the cytotoxicity assay used. Also in this case, faster means in at least 10% less time, preferably at least 20% less time and more preferably at least 50% less time. The factor that is being silenced in the first type of host cells but not in the second type of host cells is then identified as being an adenovirus inhibitory factor. In a variation of this embodiment, the first type of host cells contain more than one silencing factor, wherein the silencing factors each have a different target sequence on the same target gene.

In certain embodiments, the RNA interference by the silencing factor in the methods to identify an adenovirus inhibitory factor is done by transfecting siRNA into the first type of host cells. In another variation, the RNA interference by the silencing factor in the method to identify an adenovirus inhibitory factor is done by transfecting the first type of host cells with a plasmid vector expressing shRNA. In yet another variation, the RNA interference by the silencing factor in the method to identify an adenovirus inhibitory factor is done by transducing the first type of host cells with a viral vector expressing shRNA. Non-limiting examples of viral vectors useful in this embodiment include vectors derived from retrovirus, lentivirus, adenovirus, herpes simplex virus, simian virus 40, Epstein Barr virus, vaccinia virus and adeno associated virus.

In an embodiment, the methods to identify an adenovirus inhibitory factor are done in a functional genomics high-throughput format wherein the silencing factor is part of a library of silencing factors comprising an array of silencing factors with different target specificities. In certain variations, each component of the array comprises more than one silencing factor, wherein each silencing factor in one component of the array has a different target sequence on the same target gene.

In another embodiment, provided are methods to select a silencing factor useful for incorporation in replication-competent adenoviruses described herein, by executing a method to identify an adenovirus inhibitory factor described herein and selecting a silencing factor that after being introduced in a host cell, causes a shorter replication time or faster lytic capacity of a replication-competent adenovirus.

In an embodiment, the methods to select a silencing factor useful for incorporation in replication-competent adenoviruses described herein are done in a functional genomics high-throughput format wherein the silencing factor is part of a library of silencing factors comprising an array of silencing factors with different target specificities. In a preferred variation, each component of the array comprises more than one silencing factor, wherein each silencing factor in one component of the array has a different target sequence on the same target gene. In this variation, the methods comprise a first step in which a component of the array is selected that comprises one or more silencing factors useful for the invention and a second step in which a silencing factor useful for the invention is selected from the more than one silencing factors present in the selected component of the array.

It is to be understood that methods of identifying an adenovirus inhibitory factor or of selecting a silencing factor useful for incorporation in the replication-competent adenoviruses described herein do not necessarily require a prior knowledge of the nature of the adenovirus inhibitory factor or silencing factor, nor of the biological process(es) by which the adenovirus inhibitory factor inhibits adenovirus replication or adenovirus-induced host cell lysis. The simple fact that the adenovirus inhibitory factor delays adenovirus replication or adenovirus-induced host cell lysis or that the silencing factor accelerates adenovirus replication or adenovirus-induced host cell lysis, make them a useful adenovirus inhibitory factor or a useful silencing factor for incorporation in replication-competent adenoviruses described herein, respectively.

The invention also provides formulations comprising the replication-competent adenoviruses described herein that can be used to preserve the replication-competent adenoviruses and to administer the replication-competent adenoviruses to cells. These formulations preferably consist of the replication-competent adenovirus and a diluent. The diluent allows storage of the replication-competent adenovirus for an extended time and/or administration of the replication-competent adenovirus to cells in culture and/or cells in an animal body, where it is preferred that the animal body is a human body. It is preferred that the diluent allows storage under lyophilized conditions. It is also preferred that the diluent allows both storage and administration of the replication-competent adenovirus to cells in culture and/or cells in an animal body. It is to be understood that "to allow storage" means that during storage of the formulation, the capability of the replication-competent adenovirus to infect a cell is retained with a half-life higher than one week, where it is preferred that the half-life is more than one month, and where it is most preferred that the half-life is more than six months. Storage may be at any temperature below 40° C., but it is preferred that the temperature is between 1° C. and 10° C., or that the temperature is below minus 60° C.

It is to be understood that the administration to cells in culture and/or cells in an animal body means that the formulation and the cells are brought together resulting in introduction of the replication-competent adenovirus into the cells. It is preferred that the diluent is not toxic to the cells and to the animal body. The invention does not dictate the exact composition of the diluent, but several useful diluents for the purpose of the invention are known in the art. Non-limiting examples of diluents useful in the invention are disclosed in the incorporated WO 03/057892. Optionally, the diluent may be further supplemented with additional constituents to increase physical stability of the replication-competent adenovirus during storage, to increase the introduction into the cells, or to improve the administration of the recombinant adenoviruses to the cells in an animal body. The constituents may be different for each specific use of the formulation. Non-limiting examples of the additional constituents are disclosed in WO 03/057892.

Those skilled in the art will be able to define by proper investigation useful diluents and supplements to prepare a formulation described herein which result in the introduction of the replication-competent adenovirus into cells for each particular use of the invention and each particular method of administration described herein.

The invention furthermore provides methods to administer the formulations described herein to cells, leading to introduction of the replication-competent adenoviruses of the invention into the cells. In one variation, the methods are used to administer the formulations to cells in vitro. In another variation, the methods are used to administer the formulations to cells in vivo. The methods described herein do not differ in any way from those known in the art to administer other recombinant adenoviruses to cells. In general, the replication-competent adenoviruses of the invention are diluted to reach a useful concentration in a diluent described herein. In general, the diluent is isotonic to the conditions in an animal body, but in some cases, it may be desired to use a diluent at a non-isotonic concentration. The useful concentration of the replication-competent adenovirus will be different for each different use of the invention. Skilled artisans will be able to determine the useful concentration by experimentation.

The formulation is brought into contact with the cells under either static conditions, such as in the case of administration to cells in culture or in the case of injection into an animal tissue, or under dynamic conditions, such as in the case of injection into the blood circulation of an animal body. The formulation and the cells are brought into contact at a temperature between 0° C. and 40° C., where it is preferred that the temperature is between 30° C. and 40° C. In the case where the formulation is administered into an animal body, it is preferred that the formulation and the cells are brought into contact at the existing temperature in the animal body. In one embodiment, the administration is done at an ambient atmospheric pressure. In another embodiment, the administration is done at a pressure above atmospheric pressure. In another embodiment, the administration is done by very slow infusion, also known as Convection-Enhanced Delivery (Voges et al., *Ann. Neurol.* 54(2003):479-487; Bankiewicz et al., *Exp. Neurol.* 164(2000):2-14). Contact is maintained for a time period sufficiently long to allow introduction of the replication-competent adenoviruses into the cells.

The invention also provides compositions of a replication-competent adenovirus that comprises at least one open reading frame for a silencing factor described herein and cells in which the replication-competent adenovirus replicates. Replication-competent adenoviruses have a host range that allows replication in the cells. In a preferred embodiment, the cells are cells that have lost capacity to respond to a loss of cell-cycle checkpoint control by undergoing programmed cell death. In particular examples of this embodiment, the cells are rheumatoid arthritis cells or cancer cells. For the purpose of the invention, the terms "cancer cells" and "tumor cells" are defined as cells having lost proper cell growth control, leading to uncontrolled growth and/or replication of the cells in, e.g., a mammalian body, or to accelerated growth/replication or immortality in vitro. Thus, the term includes malignant, premalignant and benign cancer cells. In a not mutually excluding preferred embodiment, the cells are human cells. In another not mutually excluding embodiment, the cells are cells in an animal body, where it is preferred that the animal body is a human body. The compositions of the invention are obtained by administering a formulation containing a replication-competent adenovirus described herein to the cells by means of a method described herein.

In certain embodiments, the cells that are part of a composition described herein are cells in a solid tumor. In one variation of these embodiments, the tumor is maintained in culture in vitro. In this embodiment, the tumor may be artificially derived from cancer cells, such as, for example, a cell line-derived spheroid, or the tumor may be derived from an explant of a tumor in an animal body. In another variation of this embodiment, the tumor is present in an animal body. In this embodiment, the tumor may be surgically implanted into the animal body or the tumor may have arisen from the animal body. In the latter case, it is preferred that the animal body is a human body.

In this embodiment, it is preferred that the short replication time and/or fast lytic capacity result in an accelerated lateral spread by the replication-competent adenoviruses from infected cells to neighboring cells in the tumor, compared to replication-competent adenoviruses lacking the silencing factor described herein. In this aspect of the invention, it is furthermore preferred that the short replication time, fast lytic capacity and/or accelerated lateral spread lead to a more effective destruction or growth inhibition of the tumor.

In another embodiment, the cells that are part of a composition described herein, are rheumatoid synovium cells. In one variation of this embodiment, the rheumatoid synovium cells are maintained in culture in vitro. In another variation of this embodiment, the rheumatoid synovium cells are present in an animal body where it is preferred that the rheumatoid synovium cells are present in a chronically inflamed joint and where it is furthermore preferred that the animal body is a human body. In this embodiment of the invention, it is preferred that the short replication time and/or fast lytic capacity result in an accelerated lateral spread by the replication-competent adenoviruses from infected cells to neighboring cells in the inflamed joint, compared to replication-competent adenoviruses lacking the silencing factor described herein. In this aspect of the invention, it is furthermore preferred that the short replication time, fast lytic capacity and/or accelerated lateral spread lead to a more effective destruction or growth inhibition of the rheumatoid synovium cells.

In yet another embodiment, the cells that are part of a composition described herein, are vascular smooth muscle cells. In one variation of this embodiment, the vascular smooth muscle cells are maintained in culture in vitro. In another variation of this embodiment, the vascular smooth muscle cells are present in an animal body, where it is preferred that the vascular smooth muscle cells are present in an area of intimal hyperplasia, such as, e.g., in atherosclerosis, restenosis or vascular graft occlusion, and where it is furthermore preferred that the animal body is a human body. In this embodiment, it is preferred that the short replication time and/or fast lytic capacity result in an accelerated lateral spread by the replication-competent adenoviruses from infected cells to neighboring cells in the area of intimal hyperplasia, compared to replication-competent adenoviruses lacking the silencing factor described herein. In this aspect of the invention, it is furthermore preferred that the short replication time, fast lytic capacity and/or accelerated lateral spread lead to a more effective destruction or growth inhibition of the vascular smooth muscle cells.

The invention furthermore contemplates the use of the replication-competent adenoviruses, methods and formulations described herein for the treatment of a disease which involves inappropriate cell survival, where it is preferred that the disease is a disease in a human being. A treatment described herein will comprise administration of a replication-competent adenovirus described herein, in a formulation described herein, to diseased cells in an animal body using a method described herein. In a particular embodiment of the invention, the disease is cancer and the diseased cells are cancer cells where it is preferred that the cancer cells are part of a solid tumor or a tumor metastasis.

Depending on the type of disease and the nature of the diseased cells, a useful replication-competent adenovirus, a useful formulation and a useful route of administration will be chosen. With respect to the replication-competent adenovirus, a useful silencing factor may be chosen on the basis of prior investigation, but preferably also on the basis of knowledge of the genetic background of the disease in general, or more preferably of the genetic background of the diseased cells in particular. Useful formulation and route of administration will be chosen on the basis of knowledge on the localization of the diseased cells in the animal body, the characteristics of the diseased cells and the characteristics of other cells present in the part of the animal body to which the formulation is administered. Non-limiting examples of the route of administration include direct injection into a tissue containing diseased cells, for example, by convection-enhanced delivery, oral administration, injection into the blood circulation, inhalation, injection into a body cavity, such as the pleural or peritoneal cavity, a joint, or a brain ventricle, injection into the lumen of a part of the gastro-intestinal or urogenital tract, and application to the surface of a certain body area, such as the skin or the otolaryngeal mucosa, for example, by means of a mouth wash. If the route of administration is via injection into the blood circulation, it is preferred that the injection is done into an artery that leads to a part of the animal body that contains the diseased cells.

The invention furthermore contemplates that a treatment of a disease described herein is combined with other methods and means to kill a population of diseased cells known in the art including, but not limited to, irradiation, introduction of genes encoding toxic proteins, such as, for example, diphtheria or pseudomonas toxin, or pro-apoptotic proteins such as Apoptin or TNF-Related Apoptosis-Inducing Ligand, or pro-drug converting enzymes like thymidine kinase, cytosine deaminase or carboxylesterase, or cytokines like interleukin-2, interleukin-12 or GM-CSF, or anti-angiogenic products like endostatin or angiostatin, or fusogenic membrane proteins such as, e.g., those derived from Human Immunodeficiency Virus, coronavirus or Gibbon Ape Leukemia Virus and administration of chemical compounds, antibodies, receptor antagonists, signaling inhibitors, molecules inhibiting protein-protein interactions, such as, e.g., interaction between p53 and a p53 antagonist or between a component of the p53 pathway and a p53 pathway inhibitor, and the like. It is anticipated that such a combined treatment may result in a more effective killing of the population of diseased cells than either treatment alone. In addition, one treatment may potentiate the effect of the other treatment. For example, irradiation and certain chemical compounds are known to induce programmed cell death. Thus, such treatments may potentiate the efficient cell lysis and virus progeny release of a replication-competent adenovirus that restores programmed cell death by silencing an inhibitor of programmed cell death described herein.

Hereinafter, the invention will be further exemplified in the Examples and figures. The several examples show a number of ways to provide the replication-competent adenoviruses, formulations, methods, compositions, and uses described herein. It is to be clearly understood that the description is not meant to in any way limit the scope of the invention as was explained in general terms above. Skilled artisans will be able to transfer the teachings of the present invention to other replication-competent adenoviruses, silencing factors, formulations, methods, compositions, and uses without departing from the present invention.

EXAMPLES

Example 1

Construction of adenovirus shuttle vectors carrying a Gateway recombination destination cassette.

To construct a shuttle vector carrying a Gateway recombination destination cassette between the adenovirus E4 region and the right-hand ITR, the construct pEndK/SpeI (generously provided by Dr. R. Alemany, Institut Catalan d'Oncologia, Barcelona, Spain) was used. pEndK/SpeI was made by first digesting pTG3602 (Chartier et al., *J. Virol.* 70(1996):4805-4810) with KpnI and religating the vector fragment comprising Ad5 map units 0 to 7 and 93 to 100 to create pEndK. Next, a unique SpeI site was introduced into pEndK by changing Ad5 nucleotide 35813 from A to T by site-directed mutagenesis to create pEndK/SpeI. PEndK/SpeI carries PacI restriction sites flanking the two Ad5 ITRs. pEndK/SpeI was made compatible with the Gateway system by ligating the Gateway destination cassette rfa (Gateway Vector Conversion System; Invitrogen, Carlsbad, Calif.) as a blunt fragment into the SpeI site (filled in with Klenow polymerase). Plasmids were selected that contained the Gateway destination cassette with the coding sequence of the ccdB gene on the adenovirus R or L strand and were designated pEndK/DEST-R and pEndK/DEST-L, respectively.

To construct a shuttle vector carrying a Gateway recombination destination cassette in place of the adenovirus E3 region, the GATEWAY destination cassette rfa (from the Gateway Vector Conversion System) was first cloned into pBluescript SK(−) (Stratagene) digested with EcoRV to obtain pBSK-DEST. From this template, the DEST cassette was PCR amplified using primers 5'-GAGGTCGACGC-GATCGATAAGCTTGATATC-3' (SEQ ID NO:1) of the incorporated herein Sequence Listing) and 5'-TAGAAC-TAGTCGATCGCCCGGGCTGCAG-3' (SEQ ID NO:2) with overhanging PvuI sites and digested with PvuI. This fragment was ligated in pBHG11 (Microbix) digested with PacI to obtain pBHG11-DEST_R.

To construct a shuttle vector carrying the full-length genome of a CRAd with a Gateway recombination destination cassette in place of the adenovirus E3 region, first pEndK/SpeI (supra) was digested with EcoRV and the EcoRV-fragment comprising the fiber gene from pBHG11 was inserted to create pEndK-Fiber. Next, the HpaI-fragment containing DEST_R from pBHG11-DEST_R was inserted into HpaI-digested pEndK-Fiber to create pEndK-Fiber_DEST_R. Finally, the Fiber_DEST_R-containing SpeI fragment from pEndK-Fiber_DEST_R was inserted into pAdΔ24E3 (see Example 7) digested with SpeI to replace the E3 region and fiber gene with the DEST_R_Fiber fragment from pEndK-Fiber_DEST_R. The resulting plasmid is pAdΔ24-DEST_R.

Example 2

General method to construct plasmids with an shRNA expression cassette that can be transported into an adenovirus shuttle vector according to Example 1 by Gateway recombination.

The plasmid pSHAG-1 (Paddison et al., *Genes Dev.* 16(2002)948-958; generously provided by Dr. G. J. Hannon, Cold Spring Harbor Laboratory, New York) is used as entry clone for the GATEWAY system (Invitrogen, Carlsbad, Calif.). pSHAG-1 contains a U6 promoter-driven expression cassette flanked by the attL1 and attL2 recombination sites such that the expression cassette can be transported into destination plasmid vectors including pEndK/DEST-R, pEndK/DEST-L, pBHG11-DEST_R and pAdΔ24-DEST_R of Example 1 using the Gateway system. shRNA-encoding sequences can be introduced by ligation of pSHAG-1 digested with BseRI and BamHI with two annealed synthetic oligonucleotides with compatible overhanging DNA sequences. The first of the two oligonucleotides should be designed to contain in the 5' to 3' order: a first stretch of at least 19 and preferably no more than 29 nucleotides complementary to the target mRNA (i.e., antisense), a loop sequence, a second stretch of nucleotides of the same length and of reverse-complementary sequence to the first stretch of nucleotides, and a stretch of at least four thymidines. The second oligonucleotide should be reverse-complementary to the first oligonucleotide. Furthermore, when annealed, then double-stranded oligonucleotides should form overhanging sites compatible with BseRI and BamHI restriction sites. Depending on the choice of the sequence of 19 to 29 nucleotides, a useful shRNA for the invention directed against a target of choice can be made. For example, useful oligonucleotide sequences to target firefly luciferase are:

```
Oligonucleotide 1:
                                          (SEQ ID NO: 3)
5'-GATTCCAATTCAGCGGGAGCCACCTGATgaagcttgA
TCGGGTGGCTCTCGCTGAGTTGGAATCCATTTTTT-3'
and Oligonucleotide 2:
                                          (SEQ ID NO: 4)
5'-GATCAAAAAATGGATTCCAACTCAGCGAGAGCC
ACCCGATcaagcttcATCAGGTGGCTCCCGCTGAATTGGAATCCG-3',
``` wherein the lower case letters represent the loop sequence. Annealing of oligonucleotides 1 and 2 followed by ligation into pSHAG-1 digested with BseRI and BamHI results in the formation of pSHAG-shRNA. In the case of the luciferase-specific shRNA example, this results in pSHAG-Ffl that encodes a shRNA homologous to nucleotides 1340 to 1368 of the coding sequence of the firefly luciferase gene.

Example 3

General methods to construct adenovirus shuttle vectors carrying an shRNA expression cassette using the plasmids from Examples 1 and 2.

To construct an adenoviral shuttle vector carrying an shRNA-expression cassette inserted between the E4 region and the right-hand ITR, the shRNA expression cassette is transferred from the pSHAG-shRNA construct of Example 2 to the pEndK/DEST-R or pEndK/DEST-L plasmid of Example 1 via an in vitro GATEWAY LR recombination reaction using the GATEWAY LR Clonase enzyme mix (Invitrogen) according to the manufacturer's protocol. This results in pEndK/shRNA-R or pEndK/shRNA-L. For example, pSHAG-Ffl is recombined with pEndK/DEST-R or pEndK/DEST-L creating pEndK-Ffl-R or pEndK-Ffl-L, respectively.

To construct an adenoviral shuttle vector carrying an shRNA-expression cassette inserted in place of the E3 region, the shRNA expression cassette is transferred from the pSHAG-shRNA construct of Example 2 to the pBHG11-DEST_R plasmid of Example 1 via the same in vitro GATEWAY LR recombination reaction to create pBHG11-shRNA. To construct a plasmid carrying the full-length genome of an AdΔ24-type CRAd (Fueyo et al., *Oncogene* 19(2000):2-12) with an shRNA-expression cassette inserted in place of the adenovirus E3 region, the shRNA expression cassette is transferred from the pSHAG-shRNA construct of Example 2 to the pAdΔ24-DEST_R plasmid of Example 1 via the same in vitro GATEWAY LR recombination reaction to create pAdΔ24-shRNA.

Example 4

General methods to construct replication-competent adenoviruses expressing shRNA molecules using a plasmid according to Example 3.

The plasmids pEndK/shRNA-R and pEndK/shRNA-L can be linearized with KpnI and/or EcoRV. This separates the Ad5 map units 0 to 7 from Ad5 map units 93 to 100 with the inserted shRNA expression cassette. These linearized molecules can be recombined in bacteria, for example, in *E. coli* BJ5183, with full-length replication-competent adenovirus DNA. Full-length replication-competent adenovirus DNA can be isolated from adenovirus particles or, alternatively, can be released by digestion from a plasmid carrying a full-length replication-competent adenovirus DNA insert. Double homologous recombination then creates a plasmid with a full-length replication-competent adenovirus genome insert, in which the shRNA expression cassette is inserted between the E4 region and the right-hand ITR. It should be noted that any full-length replication-competent adenovirus can be used to insert shRNA expression cassettes according to this method, including recombinant adenoviruses with additional modifications, such as, e.g., enhanced tumor selectivity or oncolytic potential, a changed tropism or transgene insertion. It is preferred, however, that the full-length replication-competent adenovirus does not include a PacI restriction site in its genome. The complete replication-competent adenovirus genome with inserted shRNA expression cassette is subsequently released from the plasmid by PacI digestion. This DNA is transfected into human cells using, e.g., lipofectamine reagent. The resulting recombinant replication-competent adenovirus described herein is isolated and further propagated and purified according to standard cell culture and virology methods known in the art.

pBHG11-shRNA plasmids are transfected into human cells, together with pXC1 (Microbix Biosystems) or pXC1-derived plasmids with modifications of choice, e.g., in the E1 region to create CRAds including, but not limited to, the Δ24-mutation (infra), to allow homologous recombination reconstituting a complete replication-competent adenovirus genome with the shRNA expression cassette inserted in place of the E3 region. This virus can then be isolated, propagated, purified and used according to methods known in the art. The pAdΔ24-shRNA plasmid can be digested with PacI and transfected into human cells to isolate a Δ24-type CRAd with the shRNA expression cassette inserted in place of the E3 region. This virus can then also be isolated, propagated, purified and used according to methods known in the art.

Example 5

Construction of firefly luciferase-silencing conditionally replicating adenoviruses Ad5-Δ24E3-Ffl-R and Ad5-Δ24E3-Ffl-L.

The Ad5-derived conditionally replicating adenovirus (CRAd) Ad5-Δ24E3 carrying a 24-bp deletion in the pRb-binding CR2 domain in E1A (Suzuki et al., *Clin. Cancer Res.*

8(2002):3348-3359) was used as backbone to construct CRAds expressing shRNA molecules against firefly luciferase. According to the general method described in Example 4, homologous recombination was performed in *E. coli* BJ5183 between full-length Ad5-Δ24E3 viral DNA and KpnI-digested pEndK-Ffl-R or pEndK-Ffl-L (see Example 3) to form plasmids pAdΔ24E3-Ffl-R and pAdΔ24E3-Ffl-L, respectively. These plasmids were digested with PacI to release the full-length adenoviral DNA with Ffl shRNA expression cassette insert from the plasmid backbone and were transfected into human 293 cells (Graham et al., *J. Gen. Virol.* 36(1977):59-74). Ad5-Δ24E3.Ffl-R and Ad5-Δ24E3.Ffl-L CRAds were harvested and further propagated on A549 cells (obtained from the ATCC). The E1Δ24 deletion and the U6-Ffl insertion and orientation were confirmed by PCR on the final products and functional PFU titers were determined by limiting-dilution plaque titration on 293 cells according to standard techniques.

Example 6

Specific silencing of firefly luciferase by conditionally replicating adenoviruses Ad5-Δ24E3-Ffl-R and Ad5-Δ24E3-Ffl-L in human cancer cells.

In order to accurately quantify silencing efficiency and to adequately compensate for experimental variation, we employed the reporter plasmid phAR-FF-RL that expresses firefly and *Renilla* luciferase genes from the bidirectional hAR promoter (Barski et al., *Biotechniques* 36(2004):382-4, 386, 388), thus allowing normalization of firefly luciferase silencing relative to *Renilla* luciferase expression. To construct phAR-FF-RL, the hAR promoter (nt−124 to+29 relative to the transcription start site, GenBank accession number AF112482) was obtained by PCR using subcloned genomic DNA as template and primers 5'-CCAGAA GAGCTCGCAACGTGGCATCTGCTA-3' (SEQ ID NO:5) and 5'-GTTTGGAGAGCTCCTGGGCACAATGAGGC-3' (SEQ ID NO:6), creating flanking SacI sites (underlined). The PCR product was inserted in the SacI site of pGL3-basic (Promega, Madison, Wis.) with the 3'-end of the promoter towards the firefly luciferase gene, creating phAR-FF. Next, the *Renilla* luciferase cDNA was obtained by PCR using pRL-TK (Promega) as template and primers 5'-ACAAC GGTACCGAACTTAAGC TGCAG-3' (SEQ ID NO:7) and 5'-CCGAAAGGTACCACCTGGATCCTTATC-3' (SEQ ID NO:8), creating flanking KpnI sites (underlined) and inserted into the KpnI site of phAR-FF in an orientation opposite to that of the firefly luciferase gene, such that the 5'-end of the hAR promoter faces the 5' side of the *Renilla* luciferase gene.

Human non-small cell lung carcinoma A549 cells, breast carcinoma MCF-7 cells and cervix carcinoma HeLa cells were obtained from the American Type Culture Collection (Manassas, Va.). Osteosarcoma SaOs-2 cells were a kind gift of Dr. F. van Valen (Westfalische Wilhelms-Universitat, Munster, Germany). Cells were maintained in F12-supplemented DMEM with 10% fetal calf serum, 50 IU ml$^{-1}$ penicillin and 50 μg ml$^{-1}$ streptomycin (Life Technologies, Inc., Paisley, United Kingdom). The human cancer cells lines were plated at 50 to 70% confluence in 24-well plates and transfected with 50 ng phAR-FF-RL and 250 ng irrelevant plasmid pBluescript SK(−) carrier DNA (Stratagene, La Jolla, Calif.) using Lipofectamine Plus (Invitrogen) according to the manufacturer's protocol. Infections with control CRAd Ad5-Δ24E3 or with silencing CRAds Ad5-Δ24E3.Ffl-R or Ad5-Δ24E3.Ffl-L (supra) were performed at a multiplicity of infection of 500 PFU/cell for two hours at 37° C., immediately followed by transfection. Activities of firefly and *Renilla* luciferase were determined 30 hours post-infection using the Dual-Luciferase Reporter Assay System (Promega) according to the manufacturer's protocol.

On different cell lines, Ad5-Δ24E3.Ffl-R and Ad5-Δ24E3.Ffl-L each suppressed the normalized firefly luciferase expression to approximately 60% to 30% of the expression level observed after infection with the parental control CRAd Ad5-Δ24E3 (FIG. 1A). This demonstrated that shRNAs expressed from CRAds are able to suppress the expression of a target gene in host cells infected with CRAds.

Figure 1B:
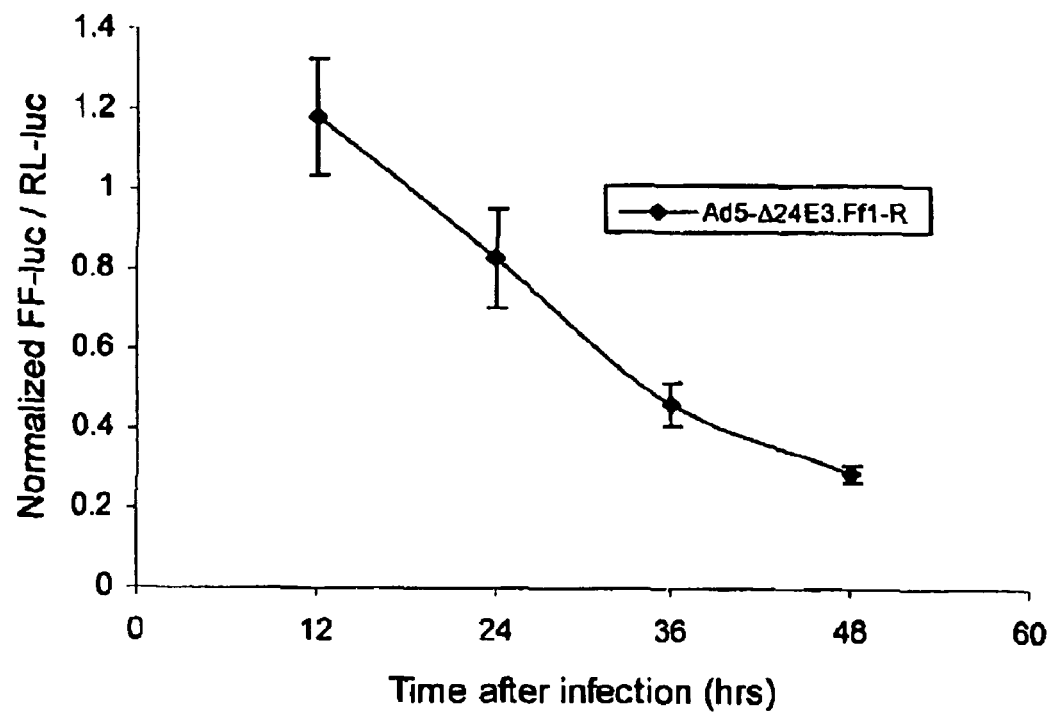
FIG. 1B. Time course of CRAd-shRNA-induced silencing of firefly luciferase in A549 cells. Cells were either infected with Ad5-Δ24E3 or with Ad5-Δ24E3.Ffl-R and analyzed at various time points after infection. At each time point, the ratio of firefly luciferase activity to Renilla luciferase activity obtained with Ad5-Δ24E3.Ffl-R was normalized to that of Ad5-Δ24E3 virus. Data shown are the mean results±SD of a representative experiment performed in triplicate.

Because the shRNAs are encoded by replicating adenoviruses, it was assumed likely that as a consequence of virus genome replication, their expression would increase in time. Pilot experiments using Ad5A24-CMV-luc (Example 10) revealed that in A549, an exponential increase in transgene expression started at 20 hours post-infection to reach a plateau at 32 hours. Assuming that the expression of the shRNAs driven by the U6-promoter follows a similar expression profile, we anticipated that the silencing effect induced by the shRNAs would increase during the replicative cycle. To test this, we performed a time-course experiment measuring the silencing by Ad5-Δ24E3.Ffl-R in A549 cells at 12, 24, 36 and 48 hours post-infection. This experiment showed that Ad5-Δ24E3.Ffl-R progressively suppressed firefly luciferase expression in A549 cells over the first two days post-infection (FIG. 1B). At 48 hours post-infection, when CPE became apparent, Ad5-Δ24E3.U6-Ffl-R had silenced firefly luciferase down to approximately 30% of the Ad5-Δ24E3 control.

Figure 1C:
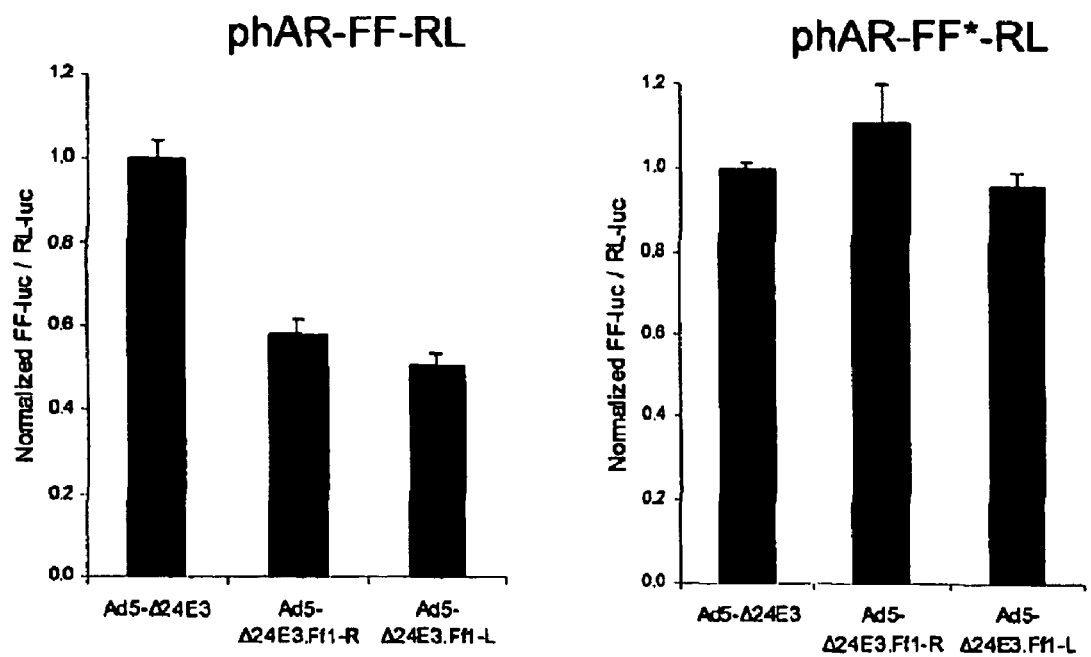
FIG. 1C. CRAd-shRNA induced silencing of firefly luciferase is sequence-specific. A549 cells were infected with the indicated CRAds immediately followed by a transfection with the reporter plasmid phAR-FF-RL or the mutated plasmid phAR-FF*-RL and analyzed as in FIG. 1A. Data shown are the mean results±SD of a representative experiment performed in triplicate.

Since the firefly luciferase expression values were normalized using *Renilla* luciferase expression as an internal control and effects of shRNA-expressing CRAds were compared to expression after infection with the Ad5-Δ24E3 parental virus, it is unlikely that the observed suppression of firefly luciferase expression was due to nonspecific effects caused by viral replication. However, to formally exclude this possibility, we investigated silencing of a mutant firefly luciferase. To this end, we introduced six silent point mutations in the shRNA target sequence in the firefly luciferase gene encoded by phAR-FF-RL. We made control reporter plasmid phAR-FF*-RL that is similar to phAR-FF-RL but contains silent mutations in the target recognition site of firefly luciferase changing the recognition sequence into: 5'-ACCAGGTTGCCCC TGCTGAGTTGGAATCG-3' (mutations are underlined) (SEQ ID NO:9). The mutations were first introduced in pGL2 (Promega) where the target recognition site is fortuitously flanked by EcoRV and ClaI restriction sites allowing the use of a small linker to introduce the mutations. For this purpose, the oligonucleotides 5'-ACCAGGTTGCCCCTGCTGAGT-TGGAAT-3' (SEQ ID NO:10) and 5'-CGATTCCAACT-CAGCAGGGGCA ACCTGGT-3' (SEQ ID NO:11) were annealed and treated with kinase. This linker was ligated into pGL2 digested with EcoRV and ClaI, replacing the unmodified target sequence. From this vector, the 765 bp SphI-SgrAI fragment containing the firefly luciferase sequence with the mutated target site was ligated into phAR-FF-RL replacing the corresponding Sphl-SgrAI region. As expected, the mutations introduced in phAR-FF*-RL did not influence the activity of the firefly luciferase protein but abolished Ffl shRNA-mediated silencing, as was confirmed by co-transfection of the mutated reporter plasmid (phAR-FF*-RL) with pSHAG-Ffl. A549 cells were infected with Ad5-Δ24E3, Ad5-Δ24E3.U6-Ffl-R, or Ad5-Δ24E3.U6-Ffl-L, followed by transfection with the reporter plasmid phAR-FF-RL or the mutated reporter plasmid phAR-FF*-RL. FIG. 1C shows that both silencing CRAds suppressed firefly luciferase expression 30 hours post-infection as before to approximately 50%, but did not change expression of mutant firefly luciferase. This confirmed that the observed silencing of firefly luciferase expression was dependent on the shRNA target sequence and is brought about via the mammalian RNAi pathway.

Example 7

Construction of conditionally replicating adenoviruses that Silence a p53 antagonist.

A derivative of Ad5-Δ24E3 (Suzuki et al., *Clin. Cancer Res.* 8(2002):3348-3359) expressing an shRNA directed against HPVI8-E6 driven by the PolIII HI promoter was made the following way. First, Ad5-Δ24E3 linear dsDNA was isolated from virions and recombined with linearized pEndK/ Spe (supra) in BJ5183 bacteria to obtain plasmid clone pAdΔ24E3, from which full-length AdΔ24E3 DNA was released by PacI digestion. Next, a synthetic double-stranded oligonucleotide consisting of a 19-nt sequence from HPV18E6 (nucleotides 385 to 403, numbering according to Cole and Danos, *J. Mol. Biol.* 193(1987):599-608), followed by a 9-nt loop linker (lower case letters) and the reverse complement of the 19-nt HPV18E6 sequence, was inserted into the plasmid pSUPER (Brummelkamp et al., *Science* 296(2002):550-553) to create pSUPER-18E6. To this end, the oligonucleotides FP_superl 8E6 (5'-gatccccCTAA-CACTGGGTTATACAAttcaagagaTTGTATA ACCCAGT-GTTAGttttggaaa-3') (SEQ ID NO:12) and RP_superl 8E6 (5'-agcttttccaaaaaCTAACACTGGGTTAT ACAAtctcttgaaT-TGTATAACCCAGTGTTAGggg-3') (SEQ ID NO:13) were annealed and ligated into BglII/HindIII digested pSUPER. pSUPER-18E6 was then digested with HindIII, overhanging ends filled with Klenow polymerase, and relegated to create an NheI site. Subsequently, it was digested with SpeI and NheI to release the H1__18E6 fragment, which was then inserted into SpeI-digested pEndK/SpeI, creating plasmid pEndK.H1__18E6. Functional silencing of HPV-18E6 resulting in a decreased inhibition of p53 activity in HPV-18 transformed human cancer cells was confirmed by transfecting pEndK.H1__18E6 together with p53-specific reporter plasmid PGI3-Luc (el-Deiry et al., *Cell* 75(1993):817-825) into HeLa cervical carcinoma cells and measuring luciferase expression. This revealed significantly higher luciferase activity than was measured following control transfection of pEndK/SpeI with PG13-luc or following transfection of PG13-Luc alone. Thus, the shRNA expressed by pEndK.H1__18E6 silenced a p53 antagonist. Next, pEndK.H1__18E6 was linearized by digestion with KpnI and EcoRV and recombined with the PacI-linearized Ad5-Δ24E3 DNA in *E. coli* BJ5183 cells. This created pAdΔ24.H1__ 18E6. PacI-linearized pAdΔ24.H1__18E6 was transfected onto 911 cells (Fallaux et al., *Hum. Gene Ther.* 7(1996):215-222) and AdΔ24.H1__18E6 virus was isolated and further propagated on A549 cells.

Several CRAds with the A24-mutation in the E1 region (Fueyo et al., *Oncogene* 19(2000):2-12), each expressing a different shRNA specific for the p53 antagonists polo-like kinase-1 (plk-1), and parc were made the following way. For both target genes, three different silencing constructs were designed that target different sequences of the target mRNA. For each silencing construct, a set of two oligonucleotides was synthesized, the sequences whereof are given below. These oligonucleotides were allowed to anneal and were inserted into pSHAG-1 digested with BseRI and BaniHI according to Example 2. The shRNA expression cassettes from the resulting pSHAG-shRNA constructs were transferred into pAdΔ24-DEST_R (Example 1) via an LR GATEWAY in vitro recombination reaction according to Example 3. Full-length clones were digested with PacI and transfected in 911 cells to obtain shRNA-expressing replication-competent adenovirus, which was further propagated on A549 cells.

The oligonucleotide sets used were:

```
for plk-1; set-A:
                                     (SEQ ID NO: 14)
5'-GGCGGCTTTGCCAAGTGCTTCTCGAGAAGCACTTG
GCAAAGCCGCCCTTTTT-3'
and (SEQ ID NO: 15)
5'-GATCAAAAAGGGCGGCTTTGCCAAGTGCTTCTCG
AGAAGCACTTGGCAAAGCCGCCCG-3';

set-B:
                                     (SEQ ID NO: 16)
5'-GCCGCCTCCCTCATCCAGAACTCGAGTTCTGGATGAGGGAG
GCGGCCTTTTT-3'
and (SEQ ID NO: 17)
5'-GATCAAAAAGGCCGCCTCCCTCATCCAGAACTCGAGTTCT
GGATGAGGGAGGCGGCCG-3';
and set-C:
                                     (SEQ ID NO: 18)
5'-ATGAAGAAGATCACCCTCCTTACTCGAGTAAGGAGGGTGA
TCTTCTTCATCTTTTT-3'
and (SEQ ID NO: 19)
5'-GATCAAAAAGATGAAGAAGATCACCCTCCTTACTCG
AGTAAGGAGGGTGATCTTCTTCATCG-3';
and for parc; set-A:
                                     (SEQ ID NO: 20)
5'-GAAGCTTTCCTCGAGATCCACTTCCTGTCATGGATC
TCGAGGAAAGCTTCCTTTTT-3'
and (SEQ ID NO: 21)
5'-GATCAAAAAGGAAGCTTTCCTCGAGATCCAT
GACAGGAAGTGGATCTCGAGGAAAGCTTCCG-3';

set-B:
                                     (SEQ ID NO: 22)
5'-GCATCGAGCAGCACATGGATCTTCCTGTCAATCCATGTGCT
GCTCGATGCCTTTTT-3'
and (SEQ ID NO: 23)
5'-GATCAAAAAGGCATCGAGCAGCACATGGATTGACAG
GAAGATCCATGTGCTGCTCGATGCCG-3';
and set-C:
                                     (SEQ ID NO: 24)
5'-CTCGCCAGGAGAAGCGGTTTCTTCCTGTCAAAACCGCTTCT
CCTGGCGAGCTTTTT-3'
and (SEQ ID NO: 25)
5'-GATCAAAAAGCTCGCCAGGAGAAGCGGTTTTGACAG
GAAGAAACCGCTTCTCCTGGCGAGCG-3'.
```

Example 8

Construction of a conditionally replicating adenovirus that silences a p53 antagonist and additionally expresses a functional factor of the p53-dependent apoptosis pathway.

A derivative of Ad5-Δ24E3 (Suzuki et al., *Clin. Cancer Res.* 8(2002):3348-3359) expressing an shRNA directed against HPV18-E6 driven by the PolIII H1 promoter and additionally expressing human p53 was made the following way. First, the plasmid pEndK/p53 was made. To this end, a derivative of pBluescript SK(-) (Stratagene, La Jolla, Calif.) lacking the EcoRV site was made by digesting pBluescript SK(-) with SmaI and EcoRV followed by self-ligation. This vector was digested with KpnI and SalI and the KpnI/SalI fragment containing the SV40 promoter-driven human p53 expression cassette from pABS.4-p53 (Van Beusechem et al., *Cancer Res.* 62 (2002):6165-6171) was inserted to create pBSK-p53. Subsequently, the KpnI site in pBSK-p53 was changed into a SpeI site. This was done by digesting pBSK-p53 with KpnI and inserting a synthetic double-stranded oligonucleotide made by annealing oligo 5'-TCAGGAC-TAGTGGAATGTAC-3' (SEQ ID NO:26) and oligo 5'-ATTCCACTAGTCCTGAGTAC-3' (SEQ ID NO:27). The 2.6 kb SV40-p53 fragment was then released by SpeI digestion and inserted into SpeI-digested pEndK/SpeI (supra). A clone with an insert in the orientation that places the SV40-p53 cassette on the adenovirus L-strand was isolated and designated pEndK/p53. Expression of functional p53 from pEndK/p53 was confirmed by transfecting pEndK/p53 or control construct pEndK/SpeI, together with p53-specific reporter plasmid PG13-Luc or with negative control plasmid MG15-Luc (el-Deiry et al., *Cell* 75(1993):817-825) into p53-null SaOs-2 osteosarcoma cells and measuring luciferase expression the next day. Transfection of pEndK/p53 resulted in a p53-specific PG-13/MG-15 ratio of 63, whereas the PG-13/MG-15 ratio after transfection of empty pEndK/SpeI vector was only 0.7. Next, pEndK/p53 was digested with ClaI and filled in with Klenow polymerase following which the HincII/SmaI fragment containing the H1-18E6 fragment from pSUPER-18E6 (supra) was inserted, creating pEndK/p53.H1_18E6. Finally, pEndK/p53.H_18E6 was linearized by digestion with KpnI and EcoRV and recombined with PacI-linearized Ad5-Δ24E3 DNA (supra) in *E. coli* BJ5183 cells to create pAdΔ24.p53(L).H1_18E6. This vector was PacI-linearized and transfected onto 911 packaging cells. AdΔ24.p53(L).H1_18E6 virus was isolated and further propagated on A549 cells.

Example 9

Construction of a conditionally replicating adenovirus that silences A p53 pathway inhibitor.

CRAds with the A24-mutation in the E1 region (Fueyo et al., *Oncogene* 19(2000):2-12) and each expressing a different shRNA specific for bcl-2 were made using the same procedure described in Example 7 to make CRAds with shRNAs for plk-1 or parc. Only different sets of oligonucleotides were used, specific for target sequences on the bcl-2 mRNA, i.e.:

set-A:
(SEQ ID NO: 28)
5'-CTGCACCTGACGCCCTTCACCTTCCTGTCAGTGAAGGGCGT
CAGGTGCAGCTTTTT-3'
and (SEQ ID NO: 29)
5'-GATCAAAAAGCTGCACCTGACGCCCTTCACTGACAG
GAAGGTGAAGGGCGTCAGGTGCAGCG-3';

set-B:
(SEQ ID NO: 30)
5'-GGAGGATTGTGGCCTTCTTTCTTCCTGTCAAAAGAAGGCCA
CAATCCTCCCTTTTT-3'
and (SEQ ID NO: 31)
5'-GATCAAAAAGGGAGGATTGTGGCCTTCTTTTGACAG
GAAGAAAGAAGGCCACAATCCTCCCG-3';
and set-C:
(SEQ ID NO: 32)
5'-GATCCAGGATAACGGAGGCTCTTCCTGTCAAGCCTCCGTTA
TCCTGGATCCTTTTT-3'
and (SEQ ID NO: 33)
5'-GATCAAAAAGGATCCAGGATAACGGAGGCTTGACAG
GAAGAGCCTCCGTTATCCTGGATCCG-3.

Example 10

Construction of a conditionally replicating adenovirus that silences a p53 antagonist and that has a changed tropism.

A derivative of Ad5-Δ24RGD (Suzuki et al., *Clin. Cancer Res.* 7(2001):120-126) expressing an shRNA directed against HPV18-E6 driven by the PolIII H1 promoter and with a modified fiber gene that expands the adenovirus tropism causing enhanced infectivity and improved oncolytic potency on many human cancer cells is made the following way. Linear full-length double-stranded Ad5-Δ24RGD DNA is isolated from Ad5-Δ24RGD viruses using a method known in the art and this DNA is recombined with KpnI/EcoRV-digested pEndK.H1_18E6 (supra) in *E. coli* BJ5183 cells to create pAdΔ24RGD.H1_18E6. Subsequently, PacI-linearized pAdΔ24RGD.H1_18E6 is transfected onto 911 packaging cells and pAdΔ24RGD.H1_18E6 virus is isolated and further propagated on A549 cells.

Example 11

Construction of the replication-competent adenovirus Ad5Δ24-SA-Luc that expresses firefly luciferase directed by the MLP and that is useful for methods to identify an adenovirus inhibitory factor and to select shRNA molecules capable of silencing the adenovirus inhibitory factor.

To construct replication-competent adenoviruses with a transgene directed by the endogenous adenovirus MLP, a splice acceptor sequence followed by a multiple cloning site and a polyadenylation site was inserted in place of the E3 region of a plasmid containing a partial Ad5 genome. To this end, synthetic oligonucleotides 5'-GGCAGGCGCAATCT-TCGCATTTCT TTTTTCCAGGAATCTAGAGATATC-GAGCTCAATAAAG-3' (SEQ ID NO:34) and 5'-AAT-TCTTTATTGAG CTCGATATCTCTAGATTCCTGGAAAAAAA-GAAATGCGAAGATTGCGCCTGCCTGCA-3'(SEQ ID NO:35) were allowed to anneal and were cloned in pABS.4 (Microbix Biosystems, Toronto, Canada) digested with EcoRI and PstI. The resulting plasmid pABS.4-SA-MCS contains a 32-nucleotide long sequence of adenovirus serotype 40 encompassing the long fiber gene splice acceptor site, a small multiple cloning site including restriction sites for XbaI, EcoRV and SacI, and a polyadenylation site and is flexibly designed to insert a transgene of choice. To construct replication-competent adenoviruses with a transgene directed by the endogenous adenovirus MLP that can be measured by a simple and quantitative method, the firefly luciferase gene was inserted into the MCS of pABS.4-SA-MCS. To this end, the cDNA of firefly luciferase was obtained by PCR using the pSP-Luc+vector (Promega) as template DNA and oligonucleotides 5'-GGGTCTAGAGCCACCATGGAAGACGC-CAAAAAC-3' (SEQ ID NO:36) and 5'-CCCGAGCTCCT-TACACGGCGATCTTTCCGC-3' (SEQ ID NO:37) which contain overhanging XbaI and ScaI sites as primers. The PCR product was digested with XbaI and SacI and ligated into pABS.4-SA-MCS digested with the same enzymes to yield pABS.4-SA-Luc. This plasmid was digested with PacI and the fragment containing SA-Luc and the kanamycin resistance gene was inserted into PacI-digested pBHG11 (Microbix Biosystems). A clone with the insert in the orientation that places the SA-Luc on the adenovirus R-strand was isolated, and the kanamycin resistance gene was subsequently removed by digestion with SwaI followed by self-ligation, yielding pBHG11-SA-Luc.

To construct a control adenovirus containing the CMV promoter instead of the SA, the human CMV promoter was released from pAdTrack (He et al., *Proc. Natl. Acad. Sci. USA* 95(1998):2509-2514) with NheI and BglII and subcloned in pBluescript SK(−)(−) (Stratagene) digested with SpeI and BamHI. Subsequently, this plasmid was digested with XbaI and PstI and the fragment containing the CMV promoter was ligated in pABS.4.SA.MCS digested with XbaI and PstI, thereby replacing the splice acceptor site with the CMV promoter. This plasmid (pABS.4-CMV-MCS) was used to construct pBHG11-CMV-Luc in a similar way as was used to obtain pBHG11-SA-Luc (supra).

Conditionally replicating adenoviruses expressing luciferase under regulation of the MLP or the CMV were made by homologous recombination in 293 cells between the pXC1 (Microbix Biosystems) derivative pXC11-Δ24, which carries a 24-bp deletion corresponding to amino acids 122 to 129 in the CR2 domain of E1A necessary for binding to the Rb protein (Fueyo et al., *Oncogene* 19(2000):2-12), with pBHG11-SA-Luc or pBHG11-CMV-Luc, respectively. This way, CRAds Ad5Δ24-SA-Luc and Ad5Δ24-CMV-Luc were generated.

Example 12

Expression of luciferase by the replication-competent adenovirus Ad5Δ24-SA-Luc in host cells is dependent on adenovirus replication.

Figure 2:
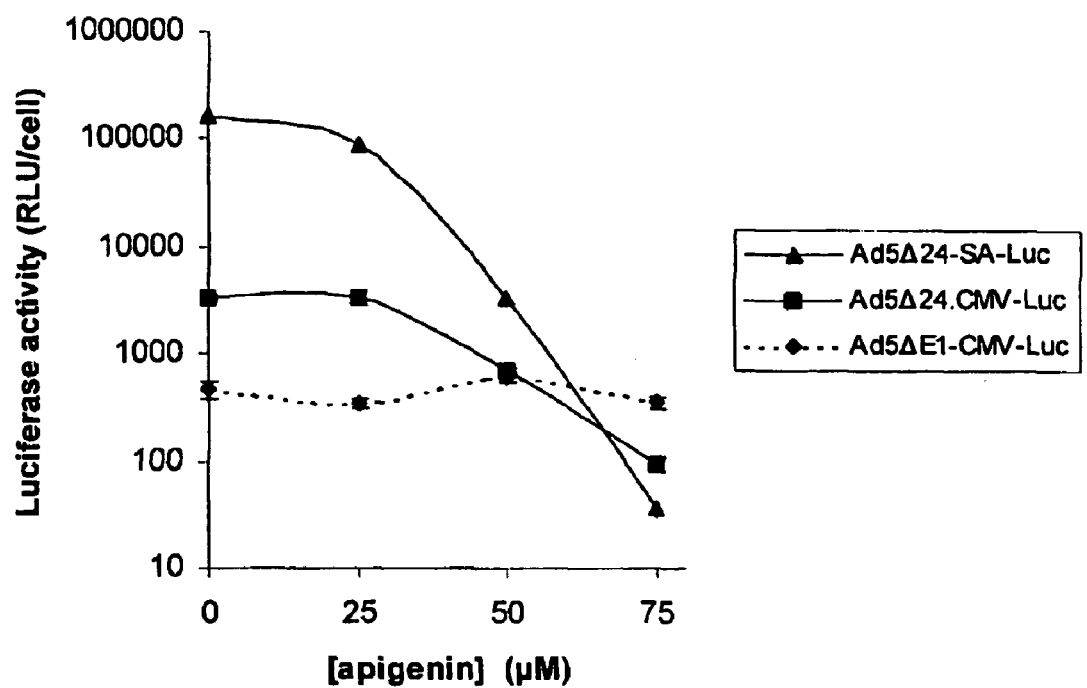
FIG. 2. Influence of cell-cycle inhibitor apigenin on luciferase expression from recombinant adenoviruses. A549 cells were infected with Ad5Δ24-SA-luc, Ad5Δ24-CMV-Luc or Ad5ΔE1-CMV-Luc at MOI 20 PFU/cell and cultured in the presence of increasing amounts of apigenin. Thirty-two hours post-infection, cells were lysed and the luciferase activities were determined. Data shown are the mean results±SD of a representative experiment performed in triplicate.

To investigate transgene expression in relation to adenovirus replication, A549 cells seeded in 96-well plates were infected with 20 PFU/cell recombinant adenovirus-expressing luciferase for two hours at 37° C., following which, the infection medium was replaced with fresh medium with or without the cell cycle inhibitor apigenin. Because adenovirus replication requires cell cycle progression through S-phase, apigenin treatment inhibits adenovirus replication. This was confirmed by the observation that at 32 hours after infection with Ad5-Δ24E3 (supra), cells cultured in the presence of 75 micromolar apigenin contained 1,000 to 10,000-fold less Ad5-Δ24E3 viral genomes as determined by quantitative PCR. The luciferase activity was measured in adenovirus-infected cells that were cultured without or with different concentrations of apigenin at 32 hours post-infection, using the luciferase chemiluminescence assay system (Promega). FIG. 2 shows the results obtained with Ad5Δ24-SA-Luc and Ad5Δ24-CMV-Luc (supra) and with replication-deficient control virus Ad5ΔE1-CMV-Luc.

Ad5-ΔE1-CMV-Luc has deleted E1 and E3 regions and an expression cassette in the E1 region consisting of the CMV promoter derived from pCEP4 (Invitrogen) and the luciferase gene from pGL3-Basic (Promega) (Yamamoto et al., *Mol. Ther.* 3(2001):385-394), generously provided by Dr. M. Yamamoto, University of Alabama at Birmingham, Ala.). Luciferase expression by the replication-deficient adenovirus vector Ad5-ΔE1-CMV-Luc was not affected by apigenin treatment, confirming that as expected, transgene expression was not dependent on adenovirus replication. Luciferase expression by the replication-competent adenovirus vector Ad5Δ24-CMV-Luc was reduced approximately 35-fold by apigenin treatment, showing that transgene expression was partially dependent ont adenovirus replication. Luciferase expression by the replication-competent adenovirus vector Ad5Δ24-SA-Luc was reduced approximately 4,600-fold by apigenin treatment, showing that the MLP-driven transgene expression in this virus was strongly dependent on adenovirus replication. Thus, Ad5Δ24-SA-Luc is a useful tool for use in methods described herein where adenovirus replication in a first type of cells is compared to adenovirus replication in a second type of cells. Luciferase activity in cells infected with Ad5Δ24-SA-Luc is directly related to replication by Ad5Δ24-SA-Luc in the cells and can be measured by simple assays (infra).

Example 13

Method to identify an adenovirus inhibitory factor and to select shRNA molecules capable of silencing the adenovirus inhibitory factor.

Inhibitory factors of adenoviral replication or lysis, as well as silencing factors capable of reducing the expression of these inhibitory factors, can be identified by silencing cellular genes in target cells using RNAi, infecting these cells with a replication-competent virus and measuring the effect of the silencing on replication and/or lysis. As mentioned in the background of the invention, large-scale silencing factor libraries are already available in the form of synthetic siRNAs or of plasmids encoding shRNAs. Methods are in place to perform large scale transfection of individual members of the library (Bems et al., *Nature* 428(2004):431-437; Paddison et al., *Nature* 428(2004):427-431), which can be readily combined with infection by a replication-competent virus according to methods known in the art. For successful identification of inhibitory factors and silencing factors using such libraries, it is preferred to use a robust and quantitative assay for measuring virus replication and/or cell lysis, which should preferably be compatible with a robotic platform to automate the screening process. To measure adenoviral replication, we developed the replication-competent Ad5Δ24-SA-Luc virus that expresses the marker gene luciferase under regulation of the major late promoter (see Example 12). Because expression of luciferase from the genome of this virus is dependent on viral replication, luciferase expression in cells infected with this virus can be used as a sensitive marker for viral replication. To measure lysis of cells infected by the virus, colorimetric, fluorometric and chemiluminescent assays for the quantification of cell death and cell lysis, based on the measurement of lactate dehydrogenase activity released from

Example 14

A conditionally replicating adenovirus according to Example 8 restores p53 function in cells expressing an adenovirus inhibitory factor being a p53 antagonist and overcomes delayed adenovirus replication and/or lysis due to expression of the adenovirus inhibitory factor in host cells.

Figure 3:
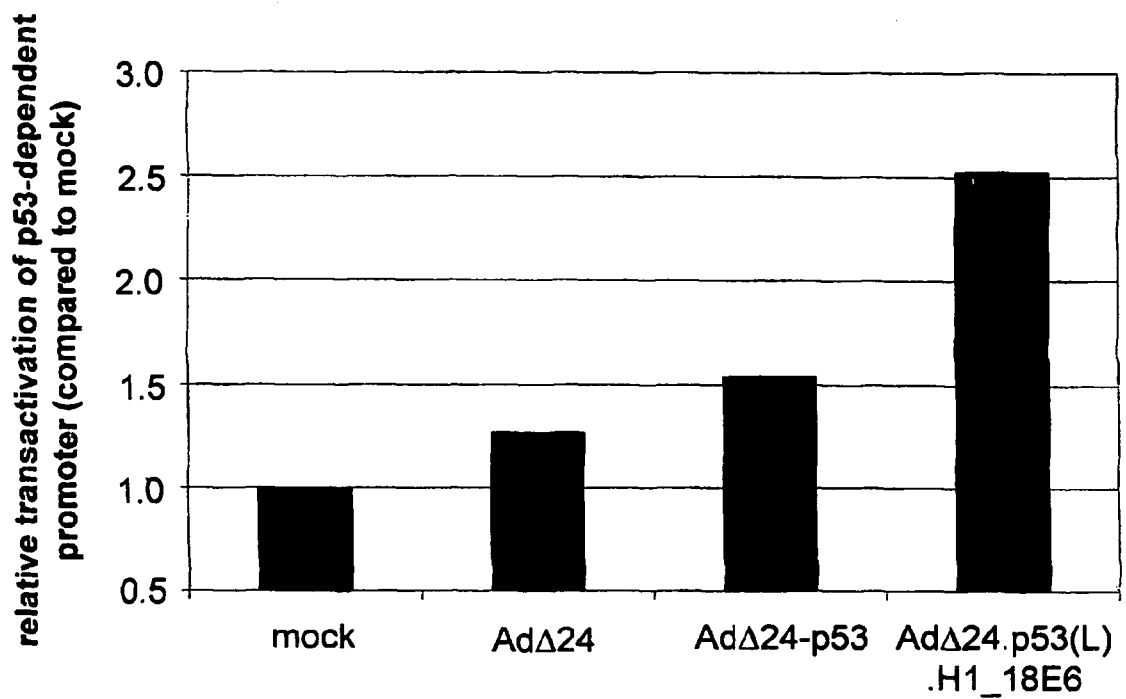
FIG. 3. Restoration of p53 function in cells expressing the p53 antagonist HPV18E6 by a replication-competent adenovirus expressing p53 and an shRNA directed against HPV18E6. HeLa HPV18-positive cervical cancer cells were transfected with p53 reporter construct PG13-Luc and 24 hours later infected with AdΔ24, AdΔ24-p53, or AdΔ24.p53(L).H1__18E6. Seventy-two hours post-infection, cells were lysed and the luciferase activities were determined. Values were normalized on the basis of mock-infected controls. Data shown are the mean results of a representative experiment performed in triplicate.

The CRAds AdΔ24 and AdΔ24-p53 (Van Beusechem et al., Cancer Res. 62(2002):6165-6171) and AdΔ24.p53(L).H1_18E6 (see Example 8) were used to infect HPV-18-positive HeLa cervical cancer cells (obtained from the ATCC) at 10 PFU/cell, 24 hours after the HeLa cells had been transfected with 200 ng PG13-Luc plasmid (el-Deiry et al., Cell 75(1993):817-825) using LipofectAMINE Plus (Invitrogen) according to the manufacturer's protocol. PG13-Luc expresses the firefly luciferase gene driven by a p53-dependent promoter. Seventy-two hours after infection, the cells were lysed in Reporter Lysis Buffer (Promega) and chemiluminescence was measured using the Luciferase Chemiluminescent Assay System (Promega) and a Lumat LB 9507 luminometer. Measured relative light units were normalized on the basis of mock-infected controls. As can be seen in FIG. 3, functional p53 expression was elevated only marginally in AdΔ24-p53-infected cells compared to AdΔ24-infected cells, showing that p53 was effectively inhibited by HPV-18E6 protein in HeLa cells. In AdΔ24.p53(L).H1_18E6-infected cells, a substantially higher level of p53 activity was measured, showing that the HPV-18E6-specific shRNA in AdΔ24.p53(L).H1_18E6 had suppressed p53 inhibition in HeLa cells.

Figure 4:
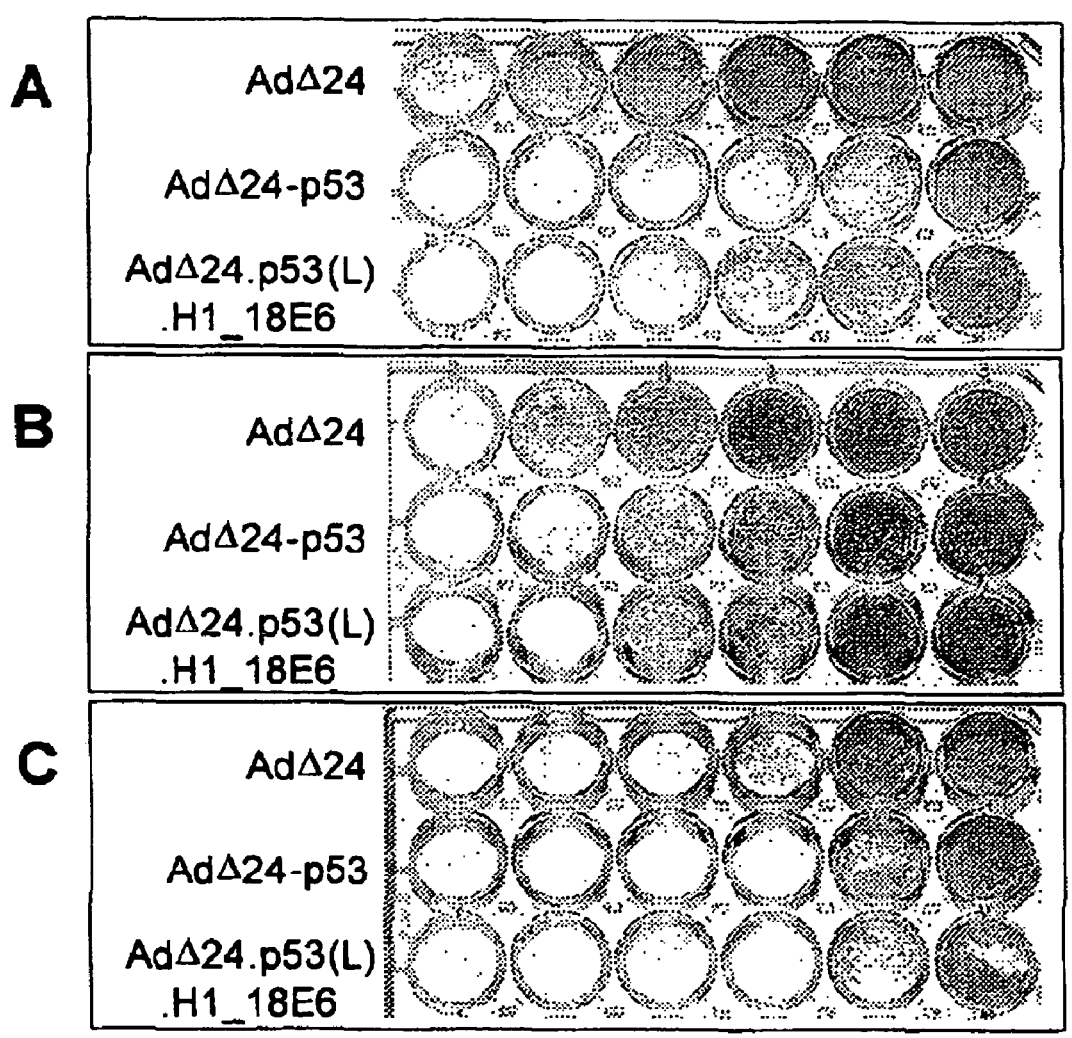
FIG. 4. Specific augmentation of adenovirus lytic replication in cells expressing the p53 antagonist HPV18E6 by a replication-competent adenovirus expressing p53 and an shRNA directed against HPV18E6. MDA-MB-231 HPV-negative cells (Panel A), SiHa HPV16-positive cells (Panel B), and HeLa HPV18-positive cells (Panel C) were infected with AdΔ24, AdΔ24-p53, or AdΔ24.p53(L).H1__18E6 at a range of virus doses as indicated. After 20 days culture, remaining cells that survived adenovirus lytic replication were stained. MOI, multiplicity of infection, i.e., number of infectious viruses per cell in the inoculum.

To investigate if silencing of HPV-18E6 by AdΔ24.p53(L).H1_18E6 would lead to specific enhancement of adenovirus replication and/or lysis in HPV-18-positive cancer cells, AdΔ24, AdΔ24-p53 and AdΔ24.p53(L).H1_18E6 were used to infect HeLa cells or HPV-16-positive SiHa cervical cancer cells (obtained from the ATCC). Since the H1_18E6 shRNA is specific for HPV-18E6 and does thus not suppress HPV-16E6, SiHa cells served as negative controls. Previously, we have found that efficacy enhancement by p53 expression in some cancer cell lines exceeds 100-fold (Van Beusechem et al., Cancer Res. 62(2002):6165-6171). One of these cell lines, breast cancer cell line MDA-MB-231, was included as positive control. Cells were seeded 5E4 per well in 24-well plates and infection was done the next day at virus doses ranging from 5 to 5E5 infectious viruses per well. After one hour, the medium was replaced and cells were subsequently cultured for 20 days with 50% medium changes every three to four days. During culture, the replication-competent adenoviruses are allowed to lyse their host cells, releasing their progeny, which can then infect new host cells. The more effective the virus life cycle (replication, cell lysis and re-infection) proceeds, the less initial virus inoculum is required to eradicate the cells in culture. After 20 days, the culture medium was removed and remaining adherent cells were fixed for 20 minutes at room temperature in 4% (v/v) formaldehyde in PBS, and stained using 10 g/l crystal violet dye in 70% (v/v) ethanol for 20 minutes at room temperature. After several washes with water, the culture plates were air dried and scanned on a Bio-Rad GS-690 imaging densitometer. FIG. 4 shows that AdΔ24-p53 was approximately 1000-times, 10-times and less than 10-times more effective against MDA-MB-231, SiHa and HeLa cells, respectively, than AdΔ24. Thus, p53 expression augmented adenovirus lytic replication in HPV-positive cervical cancer cells, but not by far as profound as in HPV-negative cancer cells. Importantly, AdΔ24.p53(L).H1_18E6 was approximately ten times more effective against HPV18-positive HeLa cells than AdΔ24-p53, but similarly effective as AdΔ24-p53 against HPV-negative MDA-MB-231 and HPV18-negative SiHa cells. This showed that expressing a short hairpin RNA silencing factor directed against an adenovirus inhibitory factor (HPV18E6) specifically relieved delayed adenovirus replication and/or lysis in host cells expressing the adenovirus inhibitory factor.

---

What is claimed is:

1. A replication-competent adenovirus having lytic capacity in target cells, the adenovirus comprising, in the genome thereof, at least one DNA sequence coding for an RNA interference molecule which reduces expression of a target gene in the target cells, said at least one DNA sequence operably linked to one or more expression control sequences wherein the target gene encodes an adenovirus inhibitory factor, and wherein the adenovirus inhibitory factor is a p53 antagonist or a p53 pathway inhibitor.

2. The replication-competent adenovirus of claim 1, wherein the RNA interference molecule comprises double-stranded RNA.

3. The replication-competent adenovirus of claim 2, wherein the double-stranded RNA comprises, per strand, between at least 19 nucleotides and less than 30 nucleotides.

4. The replication-competent adenovirus of claim 2, wherein the double-stranded RNA molecule comprises a hairpin RNA.

5. The replication-competent adenovirus of claim 1, wherein the adenovirus is a human adenovirus or an adenovirus serotype 5.

6. The replication-competent adenovirus of claim 5, wherein the adenovirus is a conditionally replicating adenovirus.

7. The replication-competent adenovirus of claim 6, wherein the adenovirus carries a mutation in the E1A region encompassing at least a part of the CR2 domain of E1A, or a deletion of amino acids 122 to 129 (LTCHEAGF) (SEQ ID NO:38) of E1A.

8. The replication-competent adenovirus of claim 1, wherein the adenovirus genome further comprises a sequence encoding at least one restoring factor that restores a p53-dependent apoptosis pathway in the target cells, operably linked to one or more expression control sequences.

9. The replication-competent adenovirus of claim 1, wherein the adenovirus inhibitory factor is selected from the group consisting of MDM2, Pirh2, COP1, Bruce, HPV-E6, herpesvirus-8 LANA, Pare, Mortalin, Plk-1, BI-1, p73DeltaN, bcl-2, bel-$x_L$, bcl-w, bfl-1, brag-1, mel-1, cIAP1, cIAP2, cIAP3, XIAP and survivin.

10. The replication-competent adenovirus of claim 1, wherein the target cells are human cells, human cancer cells, human arthritic cells, or human vascular smooth muscle cells.

11. A composition comprising the replication-competent adenovirus of claim 1, presented in a pharmaceutically acceptable form.

* * * * *

UNITED STATES PATENT AND TRADEMARK OFFICE
CERTIFICATE OF CORRECTION

PATENT NO. : 8,318,149 B2
APPLICATION NO. : 11/545095
DATED : November 27, 2012
INVENTOR(S) : Jan E. Carette et al.

It is certified that error appears in the above-identified patent and that said Letters Patent is hereby corrected as shown below:

ON THE TITLE PAGE,

Item (73) Assignee:

Now reads: "Vereniging voor christelijik hoger onderwijs, wetenschappelijk onderzoek en patientenzorg"
Should read: --Vereniging voor christelijk hoger onderwijs, wetenschappelijk onderzoek en patientenzorg--

Signed and Sealed this
Twenty-ninth Day of January, 2013

David J. Kappos
*Director of the United States Patent and Trademark Office*

UNITED STATES PATENT AND TRADEMARK OFFICE
CERTIFICATE OF CORRECTION

PATENT NO. : 8,318,149 B2
APPLICATION NO. : 11/545095
DATED : November 27, 2012
INVENTOR(S) : Carette et al.

It is certified that error appears in the above-identified patent and that said Letters Patent is hereby corrected as shown below:

IN THE SPECIFICATION:

Column 3, line 22

Now reads: "be changed to. by";

Should read: -- be changed to by --.

Column 8, line 26

Now reads: "expressed from.plasmids could";

Should read: -- expressed from plasmids could --.

Column 28, line 16

Now reads: "Ad5A24-CMV-luc";

Should read: -- Ad5Δ24-CMV-luc --.

Column 29, line 57

Now reads: "the A24-mutation in the";

Should read: -- the Δ24-mutation in the --.

Column 33, line 46

Now reads: "Ad5A24-SA-Luc and Ad5A24-CMV-Luc were";

Should read: -- Ad5Δ24-SA-Luc and Ad5Δ24-CMV-Luc were --.

Signed and Sealed this
Tenth Day of December, 2013

Margaret A. Focarino
*Commissioner for Patents of the United States Patent and Trademark Office*

CERTIFICATE OF CORRECTION (continued)
U.S. Pat. No. 8,318,149 B2

IN THE SPECIFICATION:

Column 33, line 53

Now reads: "Ad5A24-SA-Luc";

Should read: -- Ad5Δ24-SA-Luc --.